(12) United States Patent
Pitt et al.

(10) Patent No.: US 9,359,377 B2
(45) Date of Patent: Jun. 7, 2016

(54) SUBSTITUTED IMIDAZO[1,2-A]IMIDAZO[4',5':4,5] PYRROLO[1,2-D]PYRAZINES FOR TREATING RESPIRATORY SYNCYTIAL VIRUS INFECTIONS

(71) Applicant: Biota Scientific Management Pty Ltd., Notting Hill (AU)

(72) Inventors: Gary Robert William Pitt, Notting Hill (AU); Penelope Anne Mayes, Notting Hill (AU); Laura Andrau, Notting Hill (AU)

(73) Assignee: BIOTA SCIENTIFIC MANAGEMENT PTY LTD, Notting Hill, Victoria (AU)

( * ) Notice: Subject to any disclaimer, the term of this patent is extended or adjusted under 35 U.S.C. 154(b) by 0 days.

(21) Appl. No.: 14/142,666

(22) Filed: Dec. 27, 2013

(65) Prior Publication Data
US 2014/0113906 A1 Apr. 24, 2014

Related U.S. Application Data

(63) Continuation of application No. PCT/AU2012/000912, filed on Aug. 3, 2012.

(60) Provisional application No. 61/515,514, filed on Aug. 5, 2011.

(51) Int. Cl.
| | |
|---|---|
| *A61K 31/4985* | (2006.01) |
| *C07D 241/36* | (2006.01) |
| *C07D 495/22* | (2006.01) |
| *C07D 487/14* | (2006.01) |
| *C07D 471/22* | (2006.01) |
| *C07D 487/22* | (2006.01) |
| *C07D 491/22* | (2006.01) |
| *C07D 513/22* | (2006.01) |

(52) U.S. Cl.
CPC .......... *C07D 495/22* (2013.01); *A61K 31/4985* (2013.01); *C07D 471/22* (2013.01); *C07D 487/14* (2013.01); *C07D 487/22* (2013.01); *C07D 491/22* (2013.01); *C07D 513/22* (2013.01)

(58) Field of Classification Search
CPC .......................... A61K 31/4985; C07D 241/36

USPC ............................ 514/250; 544/343; 548/248
See application file for complete search history.

(56) References Cited

U.S. PATENT DOCUMENTS

| | | |
|---|---|---|
| 2010/0021458 A1 | 1/2010 | Mitchell et al. |
| 2011/0207728 A1 | 8/2011 | Mitchell et al. |
| 2012/0135998 A1 | 5/2012 | Mayes et al. |

FOREIGN PATENT DOCUMENTS

| | | | |
|---|---|---|---|
| CN | 101103029 | | 1/2008 |
| CN | 101460471 | | 6/2009 |
| WO | WO 2008/037011 | | 4/2008 |
| WO | WO 2011/094823 | | 8/2011 |
| WO | WO 2012/068622 | | 5/2012 |
| WO | WO 2013/020164 | * | 2/2013 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report Dated Feb. 11, 2014 in International Application No. PCT/AU2012/000912.
Chinese Office Action and Search Report dated Dec. 3, 2014 in Corresponding Chinese Application No. 201280035361.9.

* cited by examiner

*Primary Examiner* — Douglas M Willis
(74) *Attorney, Agent, or Firm* — B. Aaron Schulman, Esq.; Stites & Harbison, PLLC

(57) ABSTRACT

The present invention relates to compounds of formula (I) or salts, racemates, isomers and/or prodrugs thereof useful in the treatment of viral infections, in particular respiratory syncytial viral (RSV) infections. The present invention also relates to processes for preparing the compounds and intermediates used in their preparation.

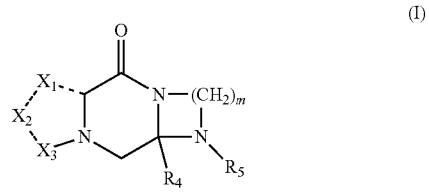

(I)

18 Claims, No Drawings

SUBSTITUTED IMIDAZO[1,2-A]IMIDAZO[4',5':4,5] PYRROLO[1,2-D]PYRAZINES FOR TREATING RESPIRATORY SYNCYTIAL VIRUS INFECTIONS

This application is a continuation of PCT/AU2012/000912, filed Aug. 3, 2012, which claims priority to U.S. Provisional Appl. No. 61/515,514, filed, Aug. 5, 2011, both of which are incorporated by reference herein.

TECHNICAL FIELD

The present invention relates to compounds useful in the treatment of viral infections, in particular respiratory syncytial viral (RSV) infections. The present invention also relates to processes for preparing the compounds and intermediates used in their preparation.

BACKGROUND

Respiratory syncytial virus (RSV) is the leading cause of acute upper and lower respiratory tract infections (LRTI) in adults, young children and infants. Although at risk populations include the hospitalized, elderly and high-risk adults, RSV is primarily considered to be a pediatric disease due to the prevalence and severity of unfavorable outcomes in infants. Acute LRTI are a leading cause of global childhood mortality and morbidity. Serological evidence indicates that in the western world approximately 95% of all children have been infected with RSV by the age of two and 100% of children have been exposed by the time they reach adulthood.

RSV is a seasonal infectious disease that generally runs from November to March/April in the Northern Hemisphere. In more tropical climates, the annual epidemics are more variable, often coinciding with the wet season. In most cases the RSV infections will only cause minor upper respiratory illness with symptoms resembling that of the common cold. However, severe infection with the virus may result in bronchiolitis or pneumonia which may result in hospitalization or death. Further, since the immune response to RSV infection is not protective, RSV infections reoccur throughout adulthood. Annual re-infection rates in adults of 3-6% have been observed.

RSV is the predominant cause of acute LRTI in infants. Symptoms of RSV infection include bronchiolitis, cough, wheezing, rales (crackling in the lungs), low grade fever (38.3° C.), decreased oral intake and in more advanced cases of infection cyanosis can occur with up to 20% of patients developing an elevated temperature. In a given year, it is estimated that in the United States alone, 4-5 million children under the age of 4 years will develop an acute RSV infection and more than 125,000 infants are hospitalized with an RSV related illness. Between 25-40% of infants with RSV infections will show signs of pneumonia and bronchiolitis. The risk and severity of RSV infections is increased in infants with, for example, chronic co-existing medical conditions such as chronic lung disease, congenital heart disease, those who have been born prematurely and those with immunodeficiency.

In adults and older children, RSV infection has been associated with upper respiratory infection, tracheobronchitis, and otitis media. However, RSV in the institutionalized elderly can be more serious and is characterized by severe pneumonia and mortality rates of up to 20 and 78%, respectively. Adults with a previous history of heart conditions, such as congestive heart failure, or lung conditions, such as chronic obstructive pulmonary disease (COPD), pneumonia and asthma are at a high risk for RSV infection as are immunocompromised adults, for example those receiving haematopoietic stem cell or lung transplants and leukemia patients.

RSV infections place a significant burden on the healthcare system. This is particularly so in the case of infants such as, for example, immunodeficient infants which on average spend twice as long in hospital as other patients with an RSV infection (7-8 days compared to 3-4 days). Hospitalization of infants with acute RSV-related bronchiolitis or RSV-related pneumonia involves supportive care management with oxygen therapy, fluids to prevent dehydration, nasal suctioning and respiratory support. There is also an economic impact associated with parents taking time away from work to care for their child.

RSV is a member of the order Mononegavirales, which consists of the non-segmented negative strand RNA viruses in the Families Paramyxoviridae, Rhabdoviridae and Filoviridae. RSV of humans (often also termed RSV or HRSV) is a member of the Pneumovirus genus of the sub-family Pneumovirinae within the Family Paramyxoviridae. Based on genetic and antigenic variations in the structural proteins, RSV is classified into two subgroups, A and B (Mufson, M. et al., J. Gen. Virol. 66:2111-2124). Other members of the Pneumovirus genus include viruses such as bovine RSV (BRSV), ovine RSV (ORSV) and pneumonia virus of mice (PVM) amongst others.

In addition to the genome features described above, family characteristics include a lipid envelope containing one or more glycoprotein species considered to be associated with attachment and entry of the host cell. Entry is considered to require a process by which the viral envelope fuses with the membrane of the host cell. Fusion of infected cells with, for example, their neighbors, can also result in the formation of fused multinucleate cells known as syncytia in some cases. The fusion process is believed to be glycoprotein mediated and is a feature shared with diverse enveloped viruses in other taxonomic groups. In the case of the Paramyxoviridae viruses of all genera characteristically express a fusion glycoprotein (F) which mediates membrane fusion.

The only small molecule drug currently approved for the treatment of severe RSV is the antiviral medication, Virazole® (ribavirin solution for inhalation). This agent has a broad spectrum antiviral with virustatic effects, and acts by inhibiting RSV replication. Unfortunately, due to its toxicity, administration of the agent is confined to a hospital setting. Its administration is further complicated by the need to follow a strict procedural process when administering the agent in order to minimize the likelihood of certain adverse effects. The agent has a number of adverse effects including sudden deterioration of respiratory function (bronchiospasm). Virazole is rarely prescribed due to its cost and potential toxicity. The efficacy of Virazole has remained controversial.

In the absence of an effective RSV antiviral therapy a number of preventative strategies have been investigated. There are no vaccines licensed for RSV but some success has been achieved in the area of prevention for infants at high risk of serious lower respiratory tract disease caused by RSV, as well as a reduction of LRTIs. One immunoglobulin-based therapy approved to protect high-risk infants from serious LRTIs is RSV-IGIV (RSV-immunoglobulin intravenous, also known as RespiGam™). RespiGam was licensed by the Food and Drug Administration in January 1996 for prevention of severe RSV lower respiratory tract disease in infants and children younger than 24 months with chronic lung disease (CLD) or a history of preterm birth (≤35 weeks' gestation). Synagis® (palivizumab) is another immunoglobulin-based therapy, more specifically, a monoclonal antibody which is indicated for the preventing RSV-related serious lower tract disease in high risk pediatric patients. In June 1998, the Food and Drug Administration approved Synagis for administration as a monthly intramuscular injection commencing before the onset of the RSV season and continuing for a total of five doses. However difficulties with administration and its high cost are prohibitive to widespread use. Further, the American Association of Pediatricians (AAP) recently updated its recommendations for use of Synagis the effect of which further restricts the use to infants at the highest risk of hospitalization during times according to likely RSV circulation. Approximately 70% of the infant population hospitalized with severe RSV disease are term infants, which in the absence of approval to treat, are not candidates for receiving Synagis.

Accordingly, there remains an ongoing need for new compounds that are useful in the treatment of RSV infections.

SUMMARY

In a first aspect there is provided a compound of formula (I):

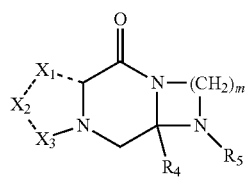

wherein

------- represents a single or a double bond as the case may be;

$X_1$ is N, $NR_3$, N—O (N-oxide), $CHR_3$ or $CR_3$;

$X_2$ is $CR_1$ or $NR_1$;

$X_3$ is $CR_2$ or $NR_2$;

$R_1$ together with $R_2$ forms an optionally substituted fused 5-membered or optionally substituted fused 6-membered ring;

$R_3$ is H or an optional substituent;

$R_4$ is optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl (including heteroaryl) or optionally substituted aryl;

$R_5$ is $R_6$, C(=O)$R_6$, C(=S)$R_6$ or S(O)$_2R_6$;

$R_6$ is selected from optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl (including heteroaryl), optionally substituted aryl, N(R")$_2$, optionally substituted (NR")$_q$(R''')$_q$$C_{3-8}$cycloalkyl, optionally substituted (NR")$_q$(R''')$_q$heterocyclyl (including heteroaryl) and optionally substituted (NR")$_q$(R''')$_q$aryl wherein each R" is independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl (including heteroaryl) and optionally substituted aryl and each R''' is independently selected from optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl (including heteroaryl) and optionally substituted aryl and each q is independently 0 or 1;

m is an integer selected from 1, 2, 3 and 4 (preferably 2), and each (CH$_2$) may be optionally substituted;

or salts, racemates, isomers and/or prodrugs thereof.

The compounds of formula (I) or salts or prodrugs thereof may be in the form of a racemate or a single stereoisomeric form.

In one embodiment, the compounds of formula (I) or salts or prodrugs thereof are in a single stereoisomeric form, more particularly, an R- or S-enantiomer.

The compounds of formula (I) are RSV antiviral agents and are useful in the treatment of RSV infections. Accordingly, the compounds of the invention are useful in the treatment of RSV disease, such as bronchiolitis or pneumonia, or in reducing exacerbation of underlying or pre-existing respiratory diseases or conditions wherein RSV infection is a cause of said exacerbation. The underlying or pre-existing respiratory diseases or conditions may include asthma, chronic obstructive pulmonary disease (COPD) and immunosuppression such as immunosuppression experienced by bone marrow transplant recipients.

In a second aspect there is provided an RSV antiviral agent comprising the compound of formula (I) defined above or its salts, racemates, isomers or prodrugs thereof.

There is also provided use of the compound of formula (I) defined above or its salts, racemates, isomers or prodrugs thereof as an RSV antiviral agent.

There is further provided the compound of formula (I) defined above or its salts, racemates, isomers or prodrugs thereof for use as an RSV antiviral agent.

The compound of formula (I) or its salts, racemates, isomers or prodrugs thereof may also be administered in the form of a composition.

In a third aspect there is provided a composition comprising the compound of formula (I) defined above or its salts, racemates, isomers or prodrugs thereof and a carrier.

In one embodiment, the composition is a pharmaceutical composition and the carrier is a pharmaceutically acceptable carrier.

In one embodiment, the agent or composition defined above also comprises one or more other RSV antiviral agents.

In a fourth aspect there is provided a method of treating an RSV infection comprising the step of administering the compound of formula (I) defined above or its salts, racemates, isomers or prodrugs thereof, or the agent or composition defined above, to a subject in need thereof.

In a fifth aspect there is provided a method of treating an RSV disease comprising the step of administering the compound of formula (I) defined above or its salts, racemates, isomers or prodrugs thereof, or the agent or composition defined above, to a subject in need thereof. There is also provided a method of reducing exacerbation of an underlying or pre-existing respiratory disease wherein RSV infection is a cause of said exacerbation comprising the step of administering the compound of formula (I) defined above or its salts, racemates, isomers or prodrugs thereof, or the agent or composition defined above, to a subject in need thereof.

There is also provided use of the compound of formula (I) defined above or its salts, racemates, isomers or prodrugs thereof, or the agent or composition defined above, in the manufacture of a medicament for treating an RSV infection or an RSV disease or reducing exacerbation of an underlying or pre-existing respiratory disease wherein RSV infection is a cause of said exacerbation.

There is further provided use of the compound of formula (I) or its salts, racemates, isomers or prodrugs thereof, or the agent or composition defined above, for treating an RSV infection or an RSV disease or reducing exacerbation of an underlying or pre-existing respiratory disease wherein RSV infection is a cause of said exacerbation.

There is still further provided the compound of formula (I) defined above or its salts, racemates, isomers or prodrugs thereof, or the agent or composition defined above, for use in treating an RSV infection or RSV disease or reducing exacerbation of an underlying or pre-existing respiratory disease wherein RSV infection is a cause of said exacerbation.

In a sixth aspect, there is provided a process for preparing the compound of formula (I) defined above comprising the step of reacting a compound of formula (II)

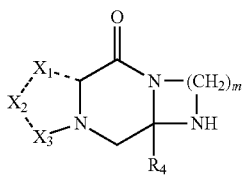
(II)

with a compound of general formula R'—C(C=O)R$_6$ where R' is a leaving group or an activated ester group; -----, $X_1$, $X_2$, $X_3$, $R_1$, $R_2$, $R_3$, $R_4$, $R_6$ and m are as previously defined; and wherein the obtained compound of formula (I) is optionally converted into a salt or prodrug thereof.

The compounds of formula (II) are also believed to be novel. Accordingly, in a seventh aspect there is provided the compound of formula (II) defined above or its salts, racemates, isomers and/or prodrugs thereof.

In one embodiment, the compounds of formula (II) are in a single stereoisomeric form, more particularly, an R- or S-enantiomer.

In one embodiment, the compound of formula (II) is prepared via cyclisation of a precursor compound of formula (III)

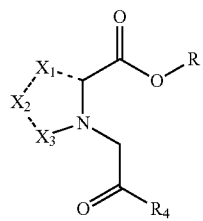
(III)

wherein R is H or $C_{1-6}$alkyl (preferably $C_{1-3}$alkyl, more preferably ethyl or methyl); and -----, $X_1$, $X_2$, $X_3$, $R_1$, $R_2$, $R_3$ and $R_4$ are as previously defined.

DETAILED DESCRIPTION

The present invention relates to compounds of formula (I) as defined above which are RSV antiviral agents and are useful in treating RSV infections or an RSV disease or reducing exacerbation of an underlying or pre-existing respiratory disease wherein RSV infection is a cause of said exacerbation.

Compounds

In one embodiment the compound of formula (I) is a compound of formula (Ia)

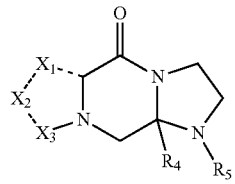
(Ia)

wherein

------- represents a single or a double bond as the case may be;

$X_1$ is N, $NR_3$, N—O, $CHR_3$ or $CR_3$;

$X_2$ is $CR_1$ or $NR_1$;

$X_3$ is $CR_2$ or $NR_2$;

$R_1$ together with $R_2$ forms an optionally substituted fused 5-membered or optionally substituted fused 6-membered aryl or heteroaryl ring;

$R_3$ is H or an optional substituent;

$R_4$ is optionally substituted heterocyclyl (including heteroaryl) or optionally substituted aryl;

$R_5$ is C(=O)$R_6$ or S(O)$_2$$R_6$, preferably C(=O)$R_6$;

$R_6$ is selected from optionally substituted $C_{1-4}$alkyl, optionally substituted $C_{3-6}$ cycloalkyl, optionally substituted heterocyclyl (including heteroaryl), optionally substituted aryl, optionally substituted (NR")$_q$(R''')$_q$$C_{3-6}$cycloalkyl, optionally substituted (NR")$_q$(R''')$_q$heterocyclyl (including heteroaryl) and optionally substituted (NR")$_q$(R''')$_q$aryl where R" is H, R''' is $C_{1-3}$alkyl (preferably methylene i.e. —CH$_2$—) and each q is independently 0 or 1;

or salts, racemates, isomers and/or prodrugs thereof;

wherein each occurrence of aryl is preferably an optionally substituted phenyl and each occurrence of heteroaryl is preferably an optionally substituted 5-membered heteroaryl containing one, two or three heteroatoms independently selected from O, N and S or an optionally substituted 6-membered heteroaryl containing one or two nitrogen atoms.

In one embodiment of the compounds of formula (I) or (Ia), $R_1$ together with $R_2$ forms an optionally substituted fused 5-membered or optionally substituted fused 6-membered heteroaryl or aryl ring and $X_1$ is N, N—O or $CR_3$ wherein $R_3$ is H or an optional substituent including but not limited to $C_{1-6}$alkyl (preferably $C_{1-3}$alkyl, more preferably methyl), $C_{2-6}$alkenyl (preferably $C_{2-3}$alkenyl), $C_{2-6}$alkynyl (preferably $C_{2-3}$alkynyl), halo, $C_{1-6}$alkylhalo (preferably $C_{1-3}$alkylhalo, more preferably $CHF_2$ and $CF_3$), hydroxyl, $C_{1-6}$alkylhydroxyl (preferably $C_{1-3}$alkylhydroxyl, more preferably $CH_2OH$), $C_{1-6}$alkoxyl (preferably $C_{1-3}$alkoxyl, more preferably methoxy), $C_{1-6}$alkoxyhalo (preferably $C_{1-3}$alkoxyhalo, more preferably $OCHF_2$ and $OCF_3$), oxo, acyl, ketone (preferably $C_{1-3}$alkylketone), carboxylate (preferably $CO_2H$), ester (preferably $C_{1-3}$alkylester, more preferably $CO_2Me$ and $CO_2Et$), cyano, nitro, amino, substituted amino (preferably $C_{1-3}$alkylamino), disubstituted amino (preferably di$C_{1-3}$alkylamino), amido, aminoacyl, substituted amido (preferably $C_{1-3}$alkylamido), disubstituted amido (preferably di$C_{1-3}$alkylamido), thiol, $C_{1-6}$alkylthio, thioxo, sulfate (preferably $C_{1-3}$alkylsulfate), sulfonate (preferably $C_{1-3}$alkylsulfonate), sulfinyl, substituted sulfinyl (preferably $C_{1-3}$alkylsulfinyl), sulfonyl, substituted sulfonyl (preferably $C_{1-3}$alkylsulfonyl), sulfonamido, substituted sulfonamido (preferably $C_{1-3}$alkylsulfonamido) and disubstituted sulfonamido (preferably di$C_{1-3}$alkylsulfonamido) wherein each alkyl, alkenyl or alkynyl and groups containing them may be further optionally substituted.

Fused 5-membered rings may be optionally substituted and include but are not limited pyrrolyl, pyrazolyl, imidazolyl, triazolyl, tetrazolyl, oxazolyl, isoxazolyl, oxadiazolyl, furanyl, thiophenyl, thiazolyl, isothiazolyl and thiadiazolyl. In one embodiment the fused 5-membered ring is selected from an optionally substituted furanyl, optionally substituted thiophenyl, optionally substituted pyrrolyl, optionally substituted pyrazolyl and optionally substituted imidazoyl. In a further embodiment the fused 5-membered ring is selected from an optionally substituted furanyl, optionally substituted thiophenyl and an optionally substituted imidazolyl. In one embodiment the fused 5-membered ring is unsubstituted.

Fused 6-membered rings may be optionally substituted and include but are not limited to phenyl, pyridinyl, pyridazinyl, pyrimidinyl and pyrazinyl. In one embodiment the fused 6-membered ring is an optionally substituted phenyl. In another embodiment the fused 6-membered ring is an optionally substituted pyridinyl, pyridazinyl, pyrimidinyl or pyrazinyl, preferably optionally substituted pyridinyl. In one embodiment the fused 6-membered ring is unsubstituted.

In one embodiment $X_1$ is $CR_3$ wherein $R_3$ is as previously defined. In a preferred embodiment $R_3$ is H or $C_{1-3}$alkyl (preferably H or methyl, most preferably H).

In another embodiment $X_1$ is N.

In one embodiment $X_2$ is $CR_1$ and $X_3$ is $CR_2$.

In another embodiment $X_2$ is $NR_1$ and $X_3$ is $CR_2$.

In yet another embodiment $X_2$ is $CR_1$ and $X_3$ is $NR_2$.

In one embodiment $R_4$ is optionally substituted phenyl or an optionally substituted 6-membered heteroaryl selected from pyridinyl, pyridazinyl, pyrimidinyl and pyrazinyl. In a preferred embodiment $R_4$ is an optionally substituted phenyl or optionally substituted pyridinyl, more preferably optionally substituted phenyl and most preferably an optionally substituted para-phenyl. Suitable optional substituents include but are not limited to $C_{1-6}$alkyl (preferably $C_{1-3}$alkyl, more preferably methyl), $C_{2-6}$alkenyl (preferably $C_{2-3}$alkenyl), $C_{2-6}$alkynyl (preferably $C_{2-3}$alkynyl), $C_{3-6}$cycloalkyl, 5-membered and 6-membered heterocyclyl (including heteroaryl), aryl (preferably phenyl), halo, $C_{1-6}$alkylhalo (preferably $C_{1-3}$alkylhalo, more preferably $CHF_2$ and $CF_3$), hydroxyl, $C_{1-6}$alkylhydroxyl (preferably $C_{1-3}$alkylhydroxyl, more preferably $CH_2OH$), $C_{1-6}$alkoxyl (preferably $C_{1-3}$alkoxyl, more preferably methoxy), $C_{1-6}$ alkoxylhalo (preferably $C_{1-3}$alkoxylhalo, more preferably $OCHF_2$ and $OCF_3$), oxo (=O), acyl, ketone (preferably $C_{1-3}$alkylketone), carboxylate (preferably $CO_2H$), ester (preferably $C_{1-3}$ alkylester, more preferably $CO_2Me$ and $CO_2Et$), cyano, nitro, amino, substituted amino (preferably $C_{1-3}$alkylamino), disubstituted amino (preferably $diC_{1-3}$alkylamino), amido, aminoacyl, substituted amido (preferably $C_{1-3}$alkylamido), disubstituted amido (preferably $diC_{1-3}$alkylamido), thiol, $C_{1-6}$alkylthio, thioxo, sulfate (preferably $C_{1-3}$alkylsulfate), sulfonate (preferably $C_{1-3}$alkylsulfonate), sulfinyl, substituted sulfinyl (preferably $C_{1-3}$alkylsulfinyl), sulfonyl, substituted sulfonyl (preferably $C_{1-3}$alkylsulfonyl), sulfonamido, substituted sulfonamido (preferably $C_{1-3}$alkylsulfonamido) and disubstituted sulfonamido (preferably $diC_{1-3}$alkylsulfonamido) wherein each alkyl, alkenyl, alkynyl, cycloalkyl, heterocylcyl (including heteroaryl) and aryl group and groups containing them may be further optionally substituted. Preferred optional substituents for $R_4$ include one, two or three, preferably one or two, and most preferably one, optional substituents independently selected from the group consisting of methyl, F, Cl, Br, $CHF_2$, $CF_3$, OH, methoxy, $OCHF_2$ and $OCF_3$ with methyl, F and methoxy being particularly preferred.

In another embodiment $R_5$ is $C(=O)R_6$ wherein $R_6$ is optionally substituted $C_{1-4}$alkyl, optionally substituted $C_{3-6}$cycloalkyl, optionally substituted heterocyclyl (including heteroaryl), optionally substituted aryl, optionally substituted NH—$C_{3-6}$cycloalkyl, optionally substituted $CH_2$—$C_{3-6}$ cycloalkyl, optionally substituted NH-heteroaryl, optionally substituted $CH_2$-heteroaryl, optionally substituted NH-aryl and optionally substituted $CH_2$-aryl or $R_5$ is $S(O)_2R_6$ wherein $R_6$ is optionally substituted aryl or $CH_2$aryl;

and further wherein each occurrence of aryl is preferably an optionally substituted phenyl and each occurrence of heteroaryl is preferably an optionally substituted 5-membered heteroaryl containing one, two or three heteroatoms independently selected from O, N and S or an optionally substituted 6-membered heteroaryl containing one or two nitrogen atoms.

$R_5$ is $C(=O)R_6$ is particularly preferred.

Optionally substituted 5-membered heterocyclyl (including heteroaryl) are particularly preferred, including optionally substituted oxazolyl, optionally substituted isoxazoyl, optionally substituted furanyl and optionally substituted pyrazolyl, most preferably optionally substituted isoxazolyl. Suitable optional substituents include but are not limited to $C_{1-6}$alkyl (preferably $C_{1-4}$alkyl, more preferably methyl), $C_{2-6}$alkenyl (preferably $C_{2-3}$alkenyl), $C_{2-6}$alkynyl (preferably $C_{2-3}$alkynyl), $C_{3-6}$cycloalkyl, 5-membered and 6-membered heterocyclyl (including heteroaryl), aryl (preferably phenyl), halo, $C_{1-6}$alkylhalo (preferably $C_{1-3}$alkylhalo, more preferably $CHF_2$ and $CF_3$), hydroxyl, $C_{1-6}$alkylhydroxyl (preferably $C_{1-3}$ alkylhydroxyl, more preferably $CH_2OH$), $C_{1-6}$alkoxyl (preferably $C_{1-3}$alkoxyl, more preferably methoxy), $C_{1-6}$alkoxyhalo (preferably $C_{1-3}$alkoxyhalo, more preferably $OCHF_2$ and $OCF_3$), oxo (=O), acyl, ketone (preferably $C_{1-3}$alkylketone), carboxylate (preferably $CO_2H$), ester (preferably $C_{1-3}$alkylester, more preferably $CO_2Me$ and $CO_2Et$), cyano, nitro, amino, substituted amino (preferably $C_{1-3}$alkylamino), disubstituted amino (preferably $diC_{1-3}$ alkylamino), amido, aminoacyl, substituted amido (preferably $C_{1-3}$alkylamido), disubstituted amido (preferably $diC_{1-3}$ alkylamido), thiol, $C_{1-6}$alkylthio, thioxo, sulfate (preferably $C_{1-3}$ alkylsulfate), sulfonate (preferably $C_{1-3}$alkylsulfonate), sulfinyl, substituted sulfinyl (preferably $C_{1-3}$alkylsulfinyl), sulfonyl, substituted sulfonyl (preferably $C_{1-3}$alkylsulfonyl), sulfonamido, substituted sulfonamido (preferably $C_{1-3}$alkylsulfonamido) and disubstituted sulfonamido (preferably $diC_{1-3}$alkylsulfonamido) wherein each alkyl, alkenyl, alkynyl, cycloalkyl, heterocylcyl (including heteroaryl) and aryl group and groups containing them may be further optionally substituted. Preferred optional substituents for $R_6$ include one, two or three, preferably one or two, optional substituents independently selected from the group consisting of $C_{1-4}$alkyl, halo, nitro, $C_{1-3}$alkylhalo, $C_{1-3}$alkoxy and $C_{1-3}$alkoxyhalo, with methyl, t-butyl, nitro, F, Cl, Br, $CHF_2$, $CF_3$, methoxy, $OCHF_2$ and $OCF_3$ being particularly preferred and $C_{1-4}$alkyl, particularly methyl, being most preferred.

In a further embodiment $R_5$ is $C(=O)R_6$ where $R_6$ is a 3-substituted isoxazol-4-yl, more preferably 3-methyl isoxazol-4-yl (also known as 3-methyl-1,2-oxazol-4-yl).

In a particular embodiment there is provided a compound of formula (Ib)

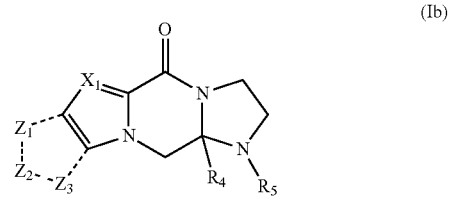

(Ib)

wherein $Z_1$, $Z_2$ and $Z_3$ are each independently selected from $CHR_7$, $CR_7$, N, $NR_7$, N—O, S and O;

each $R_7$ is independently selected from H or an optional substituent including but not limited to $C_{1-6}$alkyl (preferably $C_{1-3}$alkyl, more preferably methyl), $C_{2-6}$alkenyl (preferably $C_{2-3}$alkenyl), $C_{2-6}$alkynyl (preferably $C_{2-3}$alkynyl), halo, $C_{1-6}$alkylhalo (preferably $C_{1-3}$alkylhalo, $CHF_2$ and $CF_3$), hydroxyl, $C_{1-6}$alkylhydroxyl (preferably $C_{1-3}$alkylhydroxyl, more preferably $CH_2OH$), $C_{1-6}$alkoxyl (preferably $C_{1-3}$alkoxyl, more preferably methoxy), $C_{1-6}$alkoxyhalo (preferably $C_{1-3}$alkoxyhalo, $OCHF_2$ and $OCF_3$), oxo, acyl, ketone (preferably $C_{1-3}$alkylketone), carboxylate (preferably $CO_2H$), ester (preferably $C_{1-3}$alkylester, more preferably $CO_2Me$ and $CO_2Et$), cyano, nitro, amino, substituted amino (preferably $C_{1-3}$alkylamino), disubstituted amino (preferably $diC_{1-3}$alkylamino), amido, aminoacyl, substituted amido (preferably $C_{1-3}$ alkylamido), disubstituted amido (preferably $diC_{1-3}$alkylamido), thiol, $C_{1-6}$alkylthio, thioxo, sulfate (preferably $C_{1-3}$alkylsulfate), sulfonate (preferably $C_{1-3}$alkylsulfonate), sulfinyl, substituted sulfinyl (preferably $C_{1-3}$alkylsulfinyl), sulfonyl, substituted sulfonyl (preferably $C_{1-3}$alkylsulfonyl), sulfonamido, substituted sulfonamido (preferably $C_{1-3}$alkylsulfonamido) and disubstituted sulfonamido (preferably $diC_{1-3}$alkylsulfonamido) wherein each alkyl, alkenyl or alkynyl and groups containing them may be further optionally substituted;

-----, $X_1$, $R_3$, $R_4$, $R_5$ and $R_6$ are as previously defined;
or salts, racemates, isomers and/or prodrugs thereof.

In another particular embodiment there is provided a compound of formula (Ic)

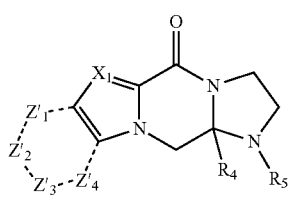

(Ic)

wherein $Z'_1$, $Z'_2$, $Z'_3$ and $Z'_4$ are each independently selected from $CHR_7$, $CR_7$, N, $NR_7$, N—O, S and O, preferably $CHR_7$, $CR_7$, N, $NR_7$ and N—O, more preferably $CHR_7$, $CR_7$, N and $NR_7$;

$R_7$ is independently selected from H or an optional substituent including but not limited to $C_{1-6}$alkyl (preferably $C_{1-3}$alkyl, more preferably methyl), $C_{2-6}$alkenyl (preferably $C_{2-3}$ alkenyl), $C_{2-6}$alkynyl (preferably $C_{2-3}$alkynyl), halo, $C_{1-6}$alkylhalo (preferably $C_{1-3}$alkylhalo, $CHF_2$ and $CF_3$), hydroxyl, $C_{1-6}$alkylhydroxyl (preferably $C_{1-3}$alkylhydroxyl, more preferably $CH_2OH$), $C_{1-6}$alkoxyl (preferably $C_{1-3}$alkoxyl, more preferably methoxy), $C_{1-6}$alkoxyhalo (preferably $C_{1-3}$alkoxyhalo, $OCHF_2$ and $OCF_3$), oxo, acyl, ketone (preferably $C_{1-3}$alkylketone), carboxylate (preferably $CO_2H$), ester (preferably $C_{1-3}$alkylester, more preferably $CO_2Me$ and $CO_2Et$), cyano, nitro, amino, substituted amino (preferably $C_{1-3}$alkylamino), disubstituted amino (preferably $diC_{1-3}$alkylamino), amido, aminoacyl, substituted amido (preferably $C_{1-3}$ alkylamido), disubstituted amido (preferably $diC_{1-3}$alkylamido), thiol, $C_{1-6}$alkylthio, thioxo, sulfate (preferably $C_{1-3}$alkylsulfate), sulfonate (preferably $C_{1-3}$alkylsulfonate), sulfinyl, substituted sulfinyl (preferably $C_{1-3}$alkylsulfinyl), sulfonyl, substituted sulfonyl (preferably $C_{1-3}$ alkylsulfonyl), sulfonamido, substituted sulfonamido (preferably $C_{1-3}$alkylsulfonamido) and disubstituted sulfonamido (preferably $diC_{1-3}$alkylsulfonamido) wherein each alkyl, alkenyl or alkynyl and groups containing them may be further optionally substituted;

-----, $X_1$, $R_3$, $R_4$, $R_5$ and $R_6$ are as previously defined;
or salts, racemates, isomers and/or prodrugs thereof.

In the case of variables $Z_1$, $Z_2$ and $Z_3$ for formula (Ib) and $Z'_1$, $Z'_2$, $Z'_3$ and $Z'_4$ for formula (Ic), each $R_7$ when present is preferably and independently selected from H, methyl, ethyl, propyl, ethenyl, propenyl, ethynyl, propynyl, F, Cl, Br, $CHF_2$, $CF_3$, OH, methoxy, ethoxy, propoxy, $OCHF_2$, $OCF_3$, oxo, carboxyl, $CO_2Me$, $CO_2Et$, $CO_2Pr$, cyano, nitro, amino, methylamino, ethylamino, propylamino, dimethylamino, diethylamino, dipropylamino, aminoacyl, amido, methylamido, ethylamido, propylamido, $diC_{1-3}$alkylamido, thiol, $C_{1-6}$ alkylthio, thioxo, SOMe, SOEt, SOPr, $SO_2Me$, $SO_2Et$, $SO_2Pr$, $NHSO_2Me$, $NHSO_2Et$, $NHSO_2Pr$, $SO_2NHMe$, $SO_2NHEt$, $SO_2NHPr$ and $SO_2NdiC_{1-3}$alkyl. H and methyl are particularly preferred $R_7$ groups.

In yet another embodiment the compound of formula (I) or (Ia) is selected from the group consisting of:

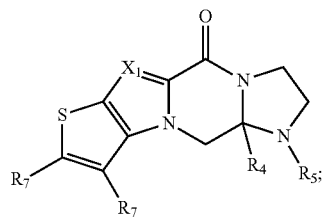

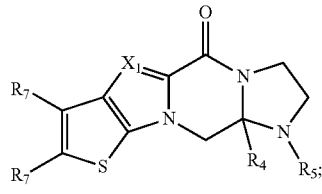

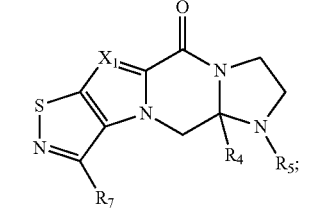

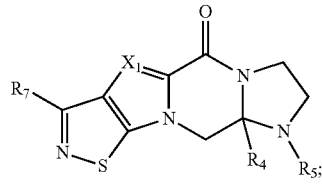

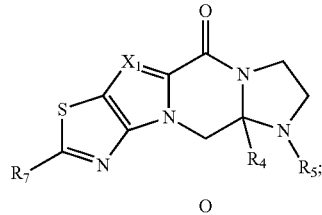

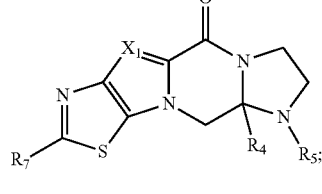

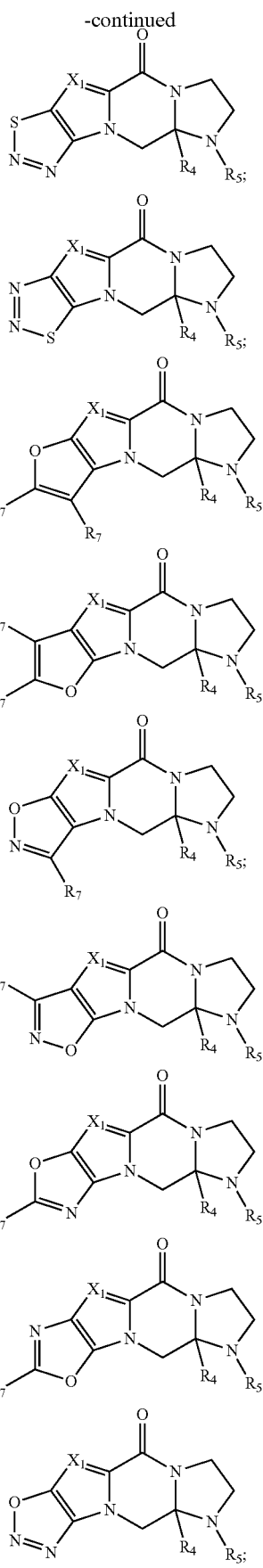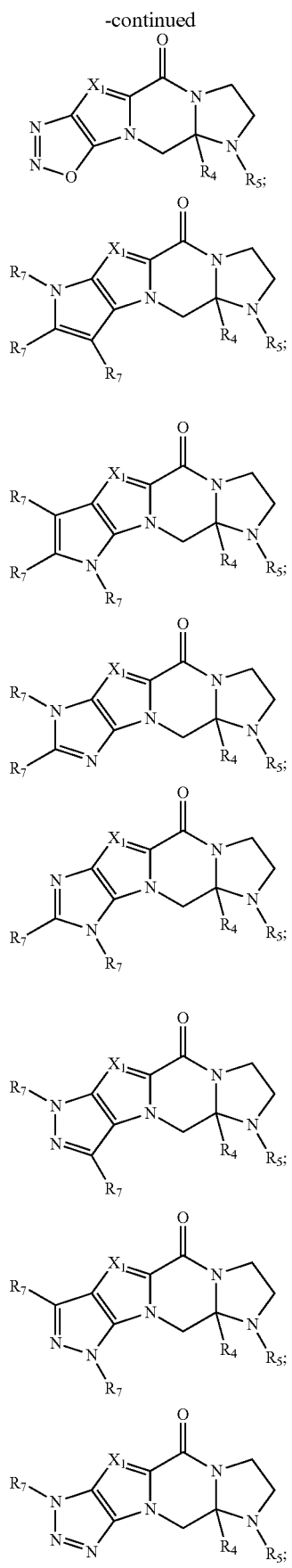

-continued

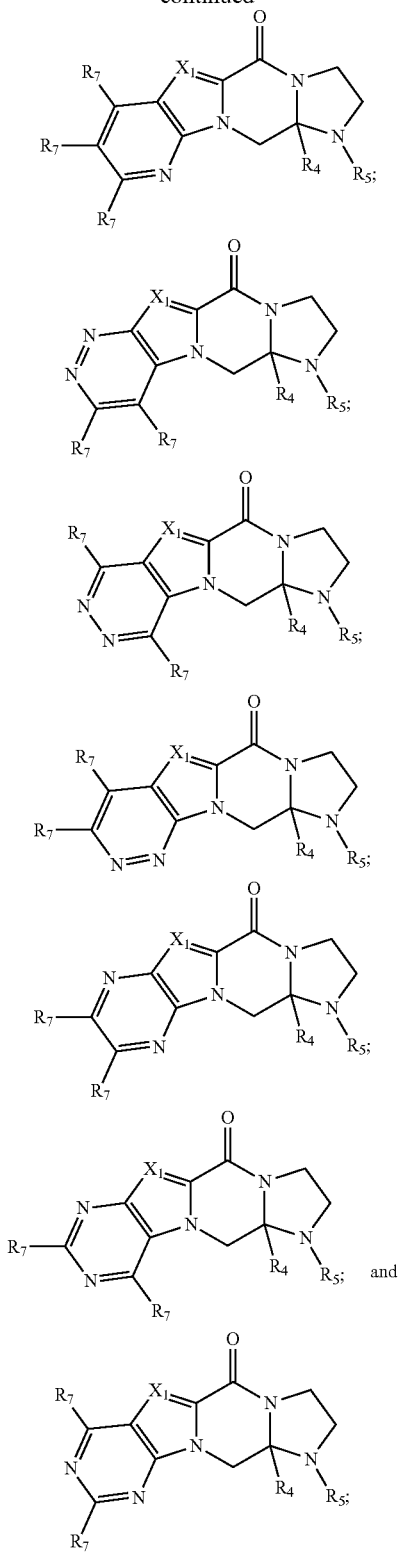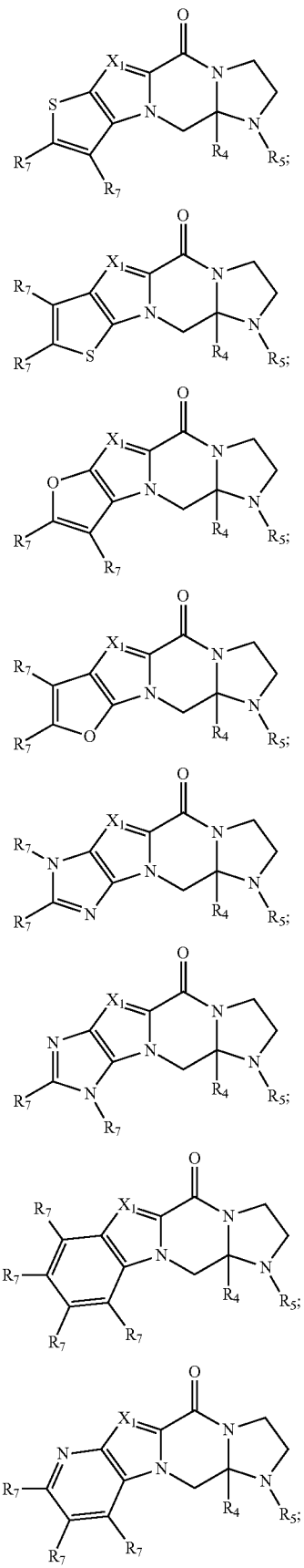
wherein $X_1$, $R_3$, $R_4$, $R_5$, $R_6$ and $R_7$ are as previously defined;
or salts, racemates, isomers and/or prodrugs thereof.
In a further embodiment the compound of formula (I) or (Ia) is selected from the group consisting of:

-continued
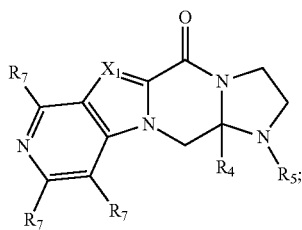
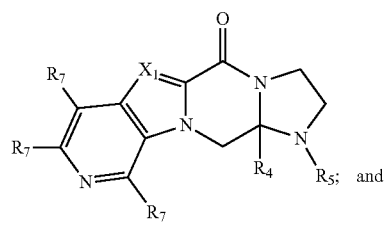
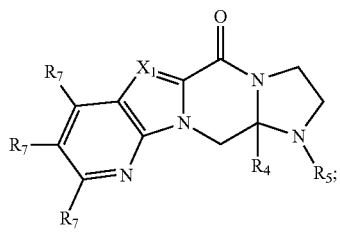
wherein $X_1$, $R_3$, $R_4$, $R_5$, $R_6$ and $R_7$ are as previously defined;
or salts, racemates, isomers and/or prodrugs thereof.
The compound of formula (I) or (Ia) may be selected from the group consisting of:
1
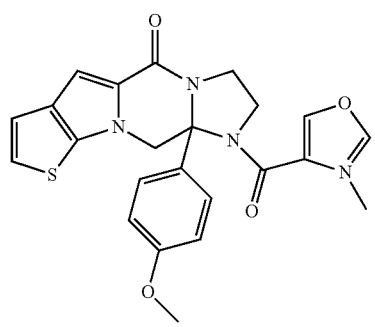
2
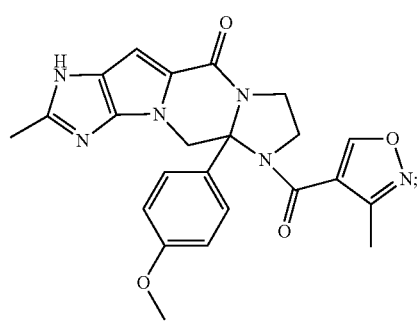
-continued
3
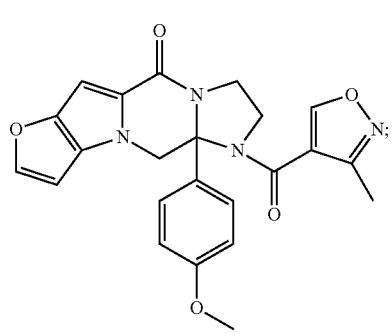
4
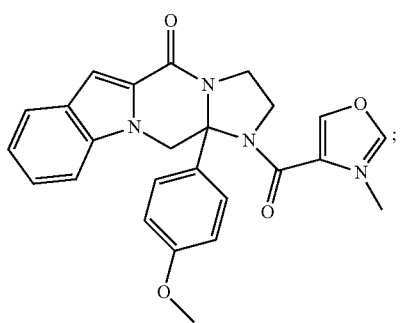
5
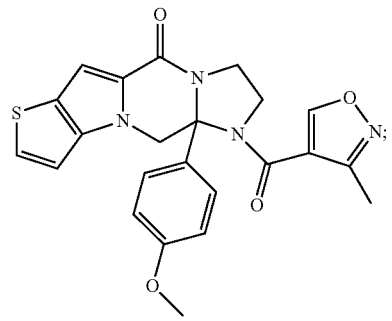
6
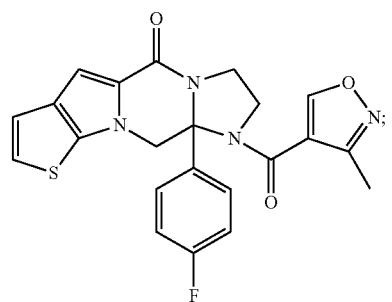
7
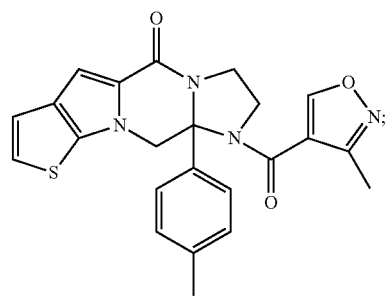

8
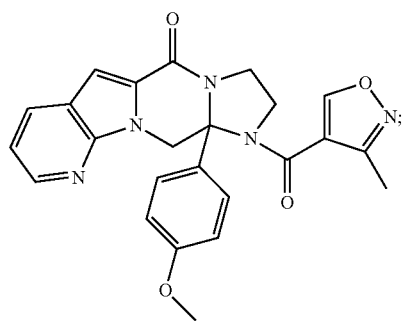
9
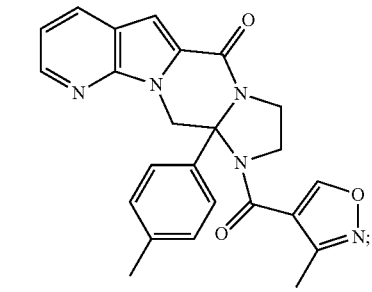
10
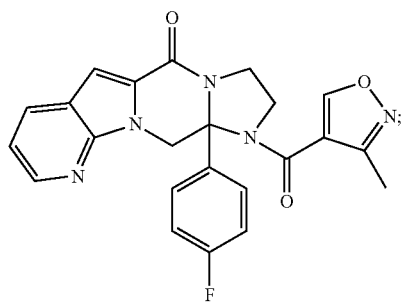
11
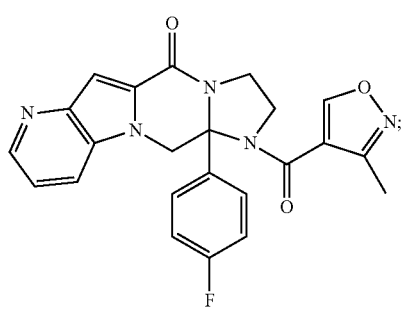
13
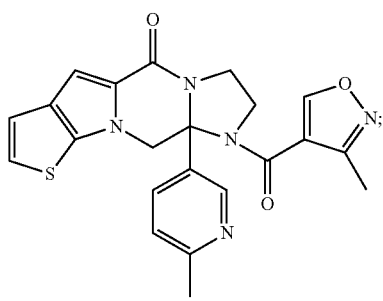
14
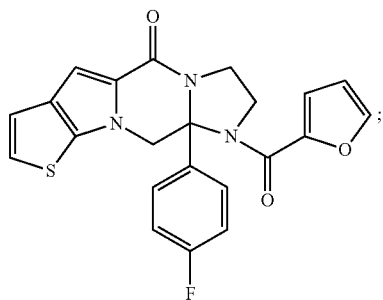
15
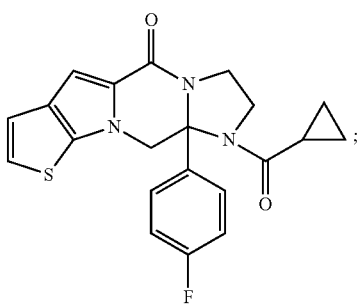
16
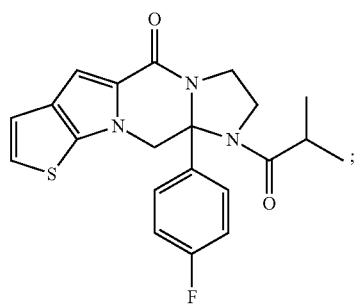

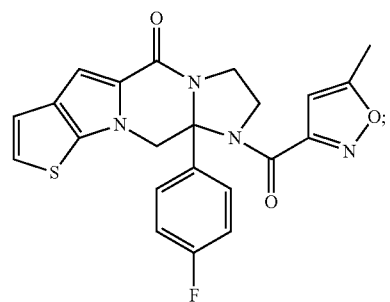
18
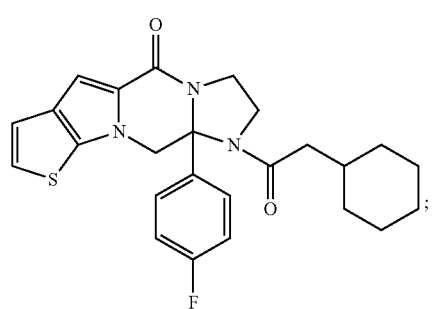
19
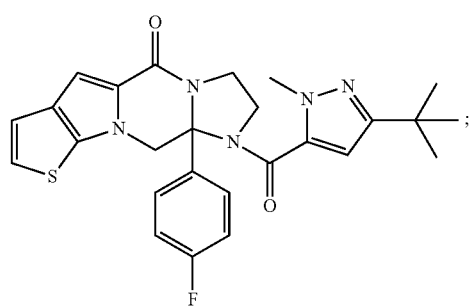
20
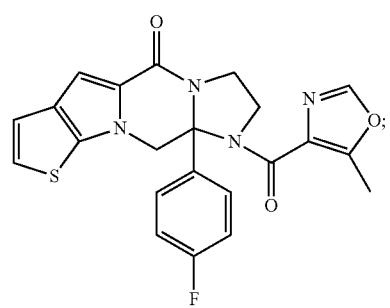
21
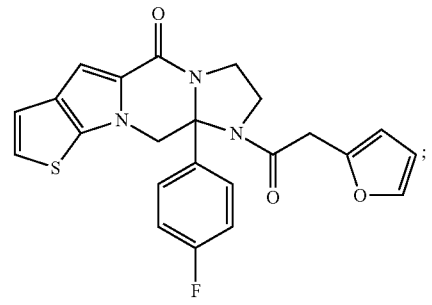
22
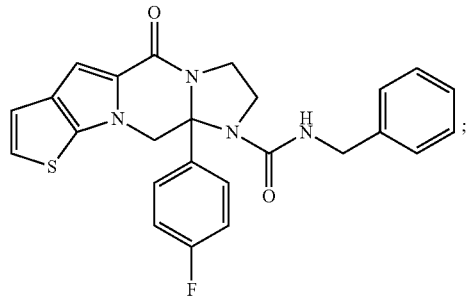
23
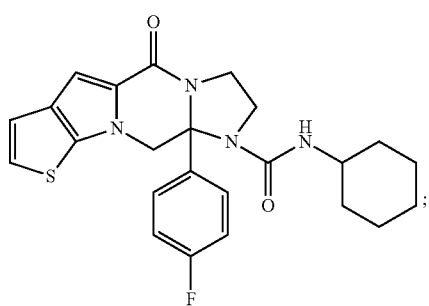
24
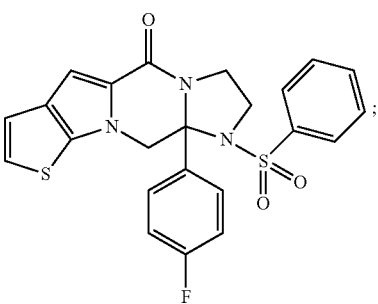
25
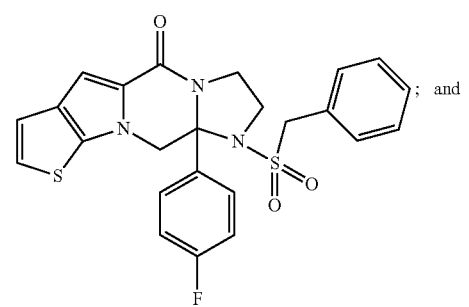
26
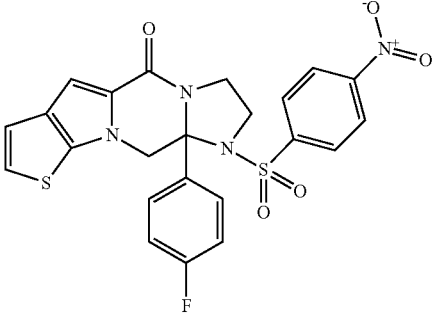
27
or salts, racemates and enantiomers thereof.

In one embodiment the compound of formula (I), (Ia), (Ib) or (Ic) is in a single stereoisomeric form, more particularly, an R- or S-enantiomer.

In a preferred embodiment, the single stereoisomeric form is an enantiomer represented by formula (I')

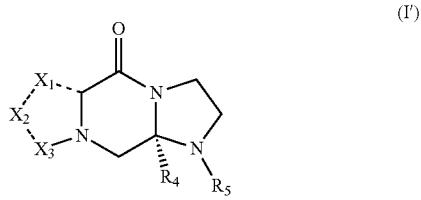

(I')

wherein -----, $X_1$, $X_2$, $X_3$, $R_1$, $R_2$, $R_3$, $R_4$, $R_5$, $R_6$ are as previously defined;

or salts and/or prodrugs thereof.

It will be understood that reference to an isomer includes stereoisomers such as enantiomers and structural isomers, such as tautomers. The term "tautomer" is used herein in its broadest sense to include compounds of formula (I) which are in a state of rapid equilibrium between two isomeric forms. Such compounds may differ in the nature of the bond connecting two atoms or groups and the position of these atoms or groups in the compound.

It will also be understood that, if it is appropriate in the context, a reference to a compound of formula (I) or (II) and embodiments thereof could refer to a compound of formula (I) or (II) per se or a salt, racemate, isomer or prodrug thereof.

The term "$C_{1-6}$alkyl" encompasses optionally substituted straight chain or branched chain hydrocarbon groups having from 1 to 6 carbon atoms. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. Such groups are also referred to as "$C_{1-6}$ alkylene" groups. $C_{1-3}$alkyl and $C_{1-3}$alkylene groups are preferred.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl, 2-methyl-2-propenyl, hexenyl, butadienyl, hexadienyl, hexatrienyl and the like. Unless the context requires otherwise, the term "$C_{1-6}$alkenyl" also encompasses alkenyl groups containing one less hydrogen atom such that the group is attached via two positions i.e. divalent. Such groups are also referred to as "$C_{2-6}$alkenylene" groups. $C_{2-3}$alkenyl and $C_{2-3}$ alkenylene groups are preferred.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and the like. Unless the context indicates otherwise, the term "$C_{2-6}$alkynyl" also encompasses alkynyl groups containing one less hydrogen atom such that the group is attached via two positions i.e. divalent. Such groups are also referred to as "$C_{2-6}$alkynylene" groups. $C_{2-3}$alkynyl and $C_{2-3}$ alkynylene groups are preferred.

The term "$C_{3-8}$cycloalkyl" refers to non-aromatic cyclic hydrocarbon groups having from 3 to 8 carbon atoms, including cyclopropyl, cyclobutyl, cyclopentyl, cyclohexyl, cyclohexenyl, cycloheptyl and the like. It will be understood that cycloalkyl groups may be saturated such as cyclohexyl or unsaturated such as cyclohexenyl. $C_{3-6}$cycloalkyl groups are preferred.

The terms "hydroxy" and "hydroxyl" refer to the group —OH.

The term "$C_{1-6}$alkylhydroxyl" refers to a $C_{1-6}$alkyl which is substituted with one or more hydroxyl groups. $C_{1-3}$alkylhydroxyl groups are preferred, such as for example, —CH$_2$OH.

The term "oxo" refers to the group =O.

The term "$C_{1-6}$alkoxyl" refers to the group refers to the group O$C_{1-6}$alkyl. Examples include methoxy, ethoxy, propoxy, isoproxy, butoxy, tert-butoxy, pentoxy and the like. The oxygen atom may be located along the hydrocarbon chain, and need not be the atom linking the group to the remainder of the compound. $C_{1-3}$alkoxyl groups are preferred.

The term "aryloxy" refers to the group —Oaryl and may include variations thereof such as "alkoxyaryl", wherein aryl is defined herein. Examples include, but are not limited to, phenoxy and naphthoxy and benzyloxy.

The terms "halo", "halogen", "halogenated" and similar terms refers to fluoro, chloro, bromo and iodo (F, Cl, Br, I).

The term "$C_{1-6}$alkylhalo" refers to a $C_{1-6}$alkyl which is substituted with one or more halogens. $C_{1-3}$alkylhalo groups are preferred, such as for example, —CHF$_2$ and —CF$_3$.

The term "$C_{1-6}$alkoxylhalo" refers to a $C_{1-6}$alkoxyl which is substituted with one or more halogens. $C_{1-3}$alkoxylhalo groups are preferred, such as for example, —OCHF$_2$ and —OCF$_3$.

The term "carboxylate" or "carboxyl" refers to the group —COO$^-$ or —COOH.

The term "ester" refers to a carboxyl group having the hydrogen replaced with, for example a $C_{1-6}$alkyl group ("carboxyl$C_{1-6}$alkyl" or "$C_{1-6}$alkylester"), an aryl or aralkyl group ("arylester" or "aralkylester") and so on. $C_{1-3}$alkylester groups are preferred, such as for example, methylester (—CO$_2$Me), ethylester (—CO$_2$Et) and propylester (—CO$_2$Pr) and includes reverse esters thereof (e.g. —OCOMe, —OCOEt and —OCOPr).

The term "cyano" refers to the group —CN.

The term "nitro" refers to the group —NO$_2$.

The term "amino" refers to the group —NH$_2$.

The term "substituted amino" or "secondary amino" refers to an amino group having a hydrogen replaced with, for example a $C_{1-6}$alkyl group ("$C_{1-6}$alkylamino"), an aryl or aralkyl group ("arylamino" or "aralkylamino") and so on. $C_{1-3}$alkylamino groups are preferred, such as for example, methylamino (—NHMe), ethylamino (—NHEt) and propylamino (—NHPr).

The term "disubstituted amino" or "tertiary amino" refers to an amino group having the two hydrogens replaced with, for example a $C_{1-6}$alkyl group, which may be the same or different ("di$C_{1-6}$alkylamino"), an aryl and $C_{1-6}$alkyl group ("aryl($C_{1-6}$alkyl)amino") and so on. Di$C_{1-3}$alkylamino groups are preferred, such as for example, dimethylamino (—NMe$_2$), diethylamino (—NEt$_2$), dipropylamino (—NPr$_2$) and variations thereof (e.g. —N(Me)(Et) and so on).

The term "acyl" or "aldehyde" refers to the group —C(=O)H.

The term "substituted acyl" or "ketone" refers to an acyl group having a hydrogen replaced with, for example a $C_{1-6}$alkyl group ("$C_{1-6}$alkylacyl" or "$C_{1-6}$alkylketone" or "keto$C_{1-6}$alkyl"), an aryl group ("arylketone"), an aralkyl group ("aralkylketone) and so on. $C_{1-3}$ alkylketone groups are preferred.

The term "amido" or "amide" refers to the group —C(O)NH$_2$.

The term "aminoacyl" refers to the group —NHC(O)H.

The term "substituted amido" or "substituted amide" refers to an amido group having a hydrogen replaced with, for example a $C_{1-6}$alkyl group ("$C_{1-6}$alkylamido" or "$C_{1-6}$ alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di$C_{1-6}$alkylamido" or "di$C_{1-6}$alkylamide"), an aralkyl and $C_{1-6}$alkyl group ("aralkyl ($C_{1-6}$alkyl)amido") and so on. Di$C_{1-3}$ alkylamide groups are preferred, such as for example, dimethylamide (—C(O)NMe$_2$), diethylamide (—C(O)NEt$_2$) and dipropylamide (—C(O)NPr$_2$) and variations thereof (e.g. —C(O)N(Me)Et and so on) and includes reverse amides thereof.

The term "thiol" refers to the group —SH.

The term "$C_{1-6}$alkylthio" refers to a thiol group having the hydrogen replaced with a $C_{1-6}$alkyl group. $C_{1-3}$alkylthio groups are preferred, such as for example, thiolmethyl, thiolethyl and thiolpropyl.

The term "thioxo" refers to the group =S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$ alkylsulfoxide"), an aryl ("arylsulfinyl"), an aralkyl ("aralkyl sulfinyl") and so on. $C_{1-3}$ alkylsulfinyl groups are preferred, such as for example, —SOmethyl, —SOethyl and —SOpropyl.

The term "sulfonyl" refers to the group —SO$_2$H.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulfonamide" refers to a sulfonylamido group having a hydrogen replaced with, for example a $C_{1-6}$alkyl group ("sulfonylamido$C_{1-6}$alkyl"), an aryl ("arylsulfonamide"), aralkyl ("aralkylsulfonamide") and so on. Sulfonylamido$C_{1-3}$alkyl groups are preferred, such as for example, —SO$_2$NHMe, —SO$_2$NHEt and —SO$_2$NHPr and includes reverse sulphonamide groups thereof (e.g. —NHSO$_2$Me, —NHSO$_2$Et and —NHSO$_2$Pr).

The term "disubstituted sufonamido" or "disubstituted sulfonamide" refers to a sulfonylamido group having the two hydrogens replaced with, for example a $C_{1-6}$alkyl group, which may be the same or different ("sulfonylamidodi$C_{1-6}$ alkyl"), an aralkyl and $C_{1-6}$alkyl group ("sulfonamido (aralkyl)$C_{1-6}$alkyl") and so on. Sulfonylamidodi$C_{1-3}$alkyl groups are preferred, such as for example, —SO$_2$NMe$_2$, —SO$_2$NEt$_2$ and —SO$_2$NPr$_2$ and variations thereof (e.g. —SO$_2$N(Me)Et and so on) and includes reserve sulphonamide groups thereof.

The term "sulfate" refers to the group —OS(O)$_2$OH and includes groups having the hydrogen replaced with, for example a $C_{1-6}$alkyl group ("$C_{1-6}$alkylsulfates"), an aryl ("arylsulfate"), an aralkyl ("aralkylsulfate") and so on. $C_{1-3}$alkylsulfate groups are preferred, such as for example, —OS(O)$_2$OMe, —OS(O)$_2$OEt and —OS(O)$_2$OPr.

The term "sulfonate" refers to the group —SO$_3$H and includes groups having the hydrogen replaced with, for example a $C_{1-6}$alkyl group ("$C_{1-6}$alkylsulfonate"), an aryl ("arylsulfonate"), an aralkyl ("aralkylsulfonate") and so on. $C_{1-3}$alkylsulfonate groups are preferred, such as for example, —SO$_3$Me, —SO$_3$Et and —SO$_3$Pr.

The term "aryl" refers to any group containing a carbocyclic (non-heterocyclic) aromatic ring and may be a mono-, bi- or tri-cyclic ring system. The aromatic ring or ring system is generally composed of 6 to 10 carbon atoms. Such groups may contain fused ring systems (such as napthyl, tetrahydronapthyl, fluorenyl, indenyl, azulenyl, anthracenyl and the like), linked ring systems (such as biphenyl groups), and may be substituted or unsubstituted. Examples of aryl groups include, but are not limited to, phenyl, biphenyl, naphthyl and tetrahydronaphthyl. Phenyl is preferred.

The term "aralkyl" refers to an aryl group substituted with a $C_{1-6}$alkyl group. Examples include benzyl and phenethyl.

The term "heterocyclyl" encompasses aromatic heterocyclyls and non-aromatic heterocyclyls. Such groups may be substituted or unsubstituted. Particularly preferred optional substituents in the case of heterocycles containing N include $C_{1-3}$alkyl particularly N—$C_{1-3}$alkyl, more preferably methyl particularly N-methyl.

The term "aromatic heterocyclyl" may be used interchangeably with the term "heteroaromatic" or the term "heteroaryl" or "hetaryl". The term "aromatic heterocyclyl" also encompasses pseudoaromatic heterocyclyls. The term "pseudoaromatic" refers to a ring system which is not strictly aromatic, but which is stabilized by means of delocalization of electrons and behaves in a similar manner to aromatic rings.

The heteroatoms in the aromatic heterocyclyl group may be selected from N, S and O.

Aromatic heterocyclyl groups may be 5-membered or 6-membered mono-cyclic aromatic ring systems.

Examples of 5-membered mono-cyclic aromatic ring systems include furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), tetrazolyl, thiadiazolyl (including 1,2,3 and 1,3,4 thiadiazolyls) and the like.

Examples of 6-membered mono-cyclic aromatic ring systems include pyridinyl, pyrimidinyl, pyridazinyl, pyrazinyl, triazinyl and the like. Examples of 6-membered aromatic heterocyclyls containing 1 nitrogen include pyridyl. Examples of 6-membered aromatic heterocyclyls containing 2 nitrogens include pyrazinyl, pyrimidinyl and pyridazinyl.

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, napthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

Examples of aromatic heterocyclyls fused to carbocyclic aromatic rings include benzothiophenyl, indolyl, isoindolyl, benzofuranyl, isobenzofuranyl, benzimidazolyl, indazolyl, benzoxazolyl, benzisoxazolyl, benzothiazolyl, benzisothiazolyl, benzimidazolyl, indazolyl, quinolinyl, isoquinolinyl, quinoxalinyl, quinazolinyl, cinnolinyl, benzotriazinyl, phthalazinyl, carbolinyl and the like.

It will be understood that suitable derivatives of aromatic heterocyclyls containing nitrogen include N-oxides thereof.

The term "non-aromatic heterocyclyl" encompasses optionally substituted saturated and unsaturated rings which contain at least one heteroatom selected from the group consisting of N, S and O.

Non-aromatic heterocyclyls may be 5-membered, 6-membered or 7-membered mono-cyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihydropyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of alkyl, alkenyl, alkynyl, cycloalkyl, hydroxyl, alkylhydroxyl, oxo, alkoxy, aryloxy, alkoxyaryl, halo, alkylhalo, alkoxyhalo, carboxylate, esters, cyano, nitro, amino, substituted amino, disubstituted amino, acyl, ketone, amido, aminoacyl, substituted amido, disubstituted amido, thiol, alkylthio, thioxo, sulfate, sulfonate, sulfinyl, substituted sulfinyl, sulfonyl, substituted sulfonyl, sulfonylamido, substituted sulfonamido, disubstituted sulfonamido, aryl, aralkyl and heterocyclyl (including heteroaryl) wherein each alkyl, alkenyl, alkynyl, cycloalkyl, aryl and heterocyclyl and groups containing them may be further optionally substituted.

The compounds of the invention may also be prepared as salts which are pharmaceutically acceptable. It will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium, alkylammonium and the like; acid addition salts of pharmaceutically acceptable inorganic acids such as hydrochloric, orthophosphoric, sulfuric, phosphoric, nitric, carbonic, boric, sulfamic, hydrobromic acids and the like; and salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulfanilic, aspartic, glutamic, edetic, stearic, palmitic, oleic, lauric, pantothenic, tannic, ascorbic, valeric, orotic acids and the like. Salts of amine groups may also comprise quaternary ammonium salts in which the amino nitrogen atom carries a suitable organic group such as an alkyl, alkenyl, alkynyl, aralkyl moiety and the like.

The salts may be formed by conventional means, such as by reacting the free base form of the compound with one or more equivalents of the appropriate acid.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water; alcoholates are formed when the solvent is alcohol. Solvates of the compounds of the present invention can be conveniently prepared or formed during the processes described herein. In addition, the compounds of the present invention can exist in unsolvated as well as solvated forms. In general, the solvated forms are considered equivalent to the unsolvated forms for the purposes of the compounds and methods provided herein.

Additionally, the compounds of the present invention can exist in unsolvated as well as solvated forms with pharmaceutically acceptable solvents such as water, ethanol and the like. The solvated forms of the compounds of the present invention are also considered to be disclosed herein.

It will be understood that compounds of formula (I) possess a chiral center and may therefore exist as a racemate or an R- or S-enantiomer. The compounds may therefore be used as a purified enantiomer or diastereomer, or as a mixture of any ratio thereof. In one embodiment there is provided a compound of formula (I) as defined above or a compound of formula (II) as defined above in a single stereoisomeric form. The isomers may be separated conventionally by chromatographic methods or using a resolving agent. Alternatively the individual isomers may be prepared by asymmetric synthesis using chiral intermediates. Where the compound has a carbon-carbon double bond, it may occur in Z- or E-form and all isomeric forms of the compounds being included in the present invention.

This invention also encompasses prodrugs of the compounds of formula (I).

The term "prodrug" is used herein in its broadest sense to include those compounds which are converted in vivo to the compound of formula (I). Use of the prodrug strategy optimizes the delivery of the drug to its site of action. Compounds having free amino, amido, hydroxyl, or carboxylic acid groups can be converted into prodrugs. Prodrugs may also include N-oxides, appropriate nitrogen atoms in compounds of formula (I).

Pharmaceutical Compositions

The invention also provides a pharmaceutical composition comprising a compound of formula (I) and a pharmaceutically acceptable carrier.

The pharmaceutical composition may further comprise or be administered in combination with one or more other RSV antiviral agents such as Virazole®.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier. Any carrier must be "pharmaceutically acceptable" meaning that it is compatible with the other ingredients of the composition and is not deleterious to a subject. The compositions of the present invention may contain other therapeutic agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours and the like) according to techniques such as those well known in the art of pharmaceutical formulation (see, for example, Remington: *The Science and Practice of Pharmacy*, 21st Ed., 2005, Lippincott Williams & Wilkins).

The pharmaceutical composition includes those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with an encapsulating material as the carrier by providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (for example, by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, for example, sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compound may be incorporated with excipients and used in the form of ingestible tablets, buccal tablets, troches, capsules, elixirs, suspensions, syrups, wafers and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin; or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, a hydrofluorocarbon (HFC) for example hydrofluoroalkanes (HFA), carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, for example gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of viral infection in living subjects having a diseased condition in which bodily health is impaired as herein disclosed in detail.

The invention also includes the compounds in the absence of carrier where the compounds are in unit dosage form.

Liquids or powders for intranasal administration, tablets or capsules for oral administration and liquids for intravenous administration are the preferred compositions.

Methods of Treatment

The compounds of formula (I) have demonstrated potency as inhibitors of RSV and therefore offer a method of treating an RSV infection. The compounds of formula (I) can also be used to treat an RSV disease or reduce exacerbation of an underlying or pre-existing respiratory disease wherein RSV infection is a cause of said exacerbation. The RSV disease may include brochiolitis or pneumonia. The underlying or pre-existing respiratory diseases or conditions may include asthma, chronic obstructive pulmonary disease (COPD) and immunosuppression such as immunosuppression experienced by bone marrow transplant recipients.

Treatment may be therapeutic treatment or prophylactic treatment. Generally, the term "treating" means affecting a subject, tissue or cell to obtain a desired pharmacological and/or physiological effect and includes: (a) inhibiting the viral infection or RSV disease, such as by arresting its development or further development; (b) relieving or ameliorating the effects of the viral infection or RSV disease, such as by causing regression of the effects of the viral infection or RSV disease; (c) reducing the incidence of the viral infection or RSV disease or (d) preventing the viral infection or RSV disease from occurring in a subject, tissue or cell predisposed to the viral infection or RSV disease or at risk thereof, but has not yet been diagnosed with a protective pharmacological and/or physiological effect so that the viral infection or RSV disease does not develop or occur in the subject, tissue or cell.

The term "subject" refers to any animal, in particular mammals such as humans, having a disease which requires treatment with the compound of formula (I). Particularly preferred treatment groups include at risk populations such as hospitalised subjects, the elderly, high-risk adults and infants.

The term "administering" should be understood to mean providing a compound or pharmaceutical composition of the invention to a subject suffering from or at risk of the disease or condition to be treated or prevented.

Although the invention has been described with reference to treating RSV infections and diseases, more particularly human and animal RSV infections or diseases, it will be appreciated that the invention may also be useful in the treatment of other viruses of the sub-family Pneumovirinae, more particularly, the genera Pneumovirus and Metapneumovirus.

Dosages

The term "therapeutically effective amount" refers to the amount of the compound of formula (I) that will elicit the biological or medical response of a subject, tissue or cell that is being sought by the researcher, veterinarian, medical doctor or other clinician.

In the treatment of RSV infections or diseases, an appropriate dosage level will generally be about 0.01 to about 500 mg per kg subject body weight per day which can be administered in single or multiple doses. The dosage may be selected, for example, to any dose within any of these ranges, for therapeutic efficacy and/or symptomatic adjustment of the dosage to the subject to be treated.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

Method of Preparation

The compounds of the invention may generally be prepared by the following method(s). Unless otherwise stated, the groups of each of the compounds are as previously defined.

Step (a): Synthesis of Precursor (Compounds of General Formula (III))

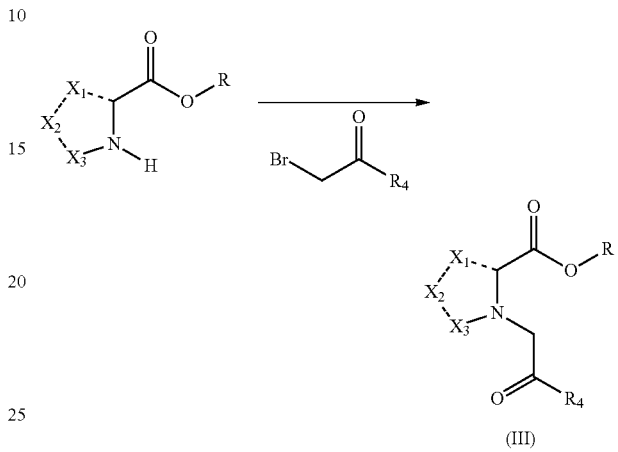

In general, one equivalent of the appropriate bicyclic ester, such as methyl 6H-thieno[2,3-b]pyrrole-5-carboxylate or methyl 2-methyl-1-[2-(trimethylsilyl)ethoxy]-1,4-dihydropyrrolo[2,3-d]imidazole-5-carboxylate, which was prepared by a modified procedure outlined by Zarghi, A.; Ebrahimabadi, A. H.; Hassanzadeh, F.; Heydari, M. R.; Shafiee, A. *Bollettino Chimico Farmaceutico*, 2003, Vol. 142, No. 6 p. 251-254), is treated with 1-2 equivalents of an appropriate base, such as sodium hydride, potassium carbonate or cesium carbonate, in a suitable organic solvent such as DMF at 0° C. The deprotonation is stirred at room temperature for approximately 1 hour. 1-2 equivalents of the appropriate bromoketone are then added at 0° C. and the reaction allowed to proceed at room temperature for at least 30 minutes. The reaction is diluted with water or sat. aq. NH$_4$Cl and the resulting precipitated product collected by filtration and used as such in the next step. If no precipitate forms, the mixture is extracted with a suitable organic solvent, such as ethyl acetate or dichloromethane and the organic layers are dried (MgSO$_4$ or Na$_2$SO$_4$) and concentrated in vacuo. The residue is purified by flash chromatography.

Step (b): Synthesis of Intermediate Via Cyclisation (Compounds of General Formula (II))

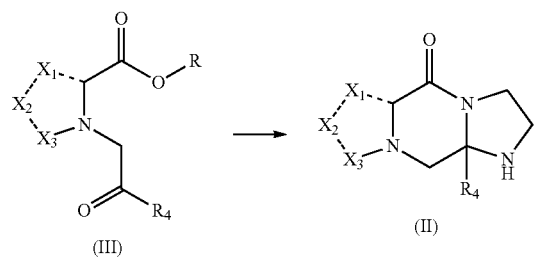

In general, one equivalent of an appropriate keto-ester or keto-acid is reacted with 3-40 equivalents of ethylenediamine. A catalytic amount of acetic acid may also be added.

The mixture is heated at reflux in an inert solvent, such as chloroform, 1,2-dichloroethane or 1,4-dioxane, and monitored by LCMS. Once complete the reaction is allowed to cool to room temperature before being concentrated in vacuo. The residue can be purified directly by flash chromatography, or suspended/dissolved in water and extracted with a suitable organic solvent such as dichloromethane. The organic layers are dried (MgSO$_4$ or Na$_2$SO$_4$) and concentrated in vacuo. The residue is then purified by flash chromatography.

Step (c): Synthesis of Final Product Via Acylation (Compounds of General Formula (I))

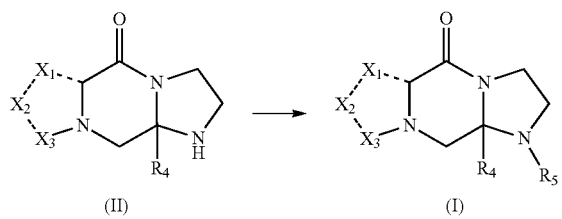

In general, one equivalent of an appropriate cyclic amine in pyridine is added to 2.5-5 equivalents of an appropriate acid chloride in pyridine at 0° C. The acid chloride is initially prepared by reacting the corresponding acid with thionyl chloride or with oxalyl chloride and catalytic DMF in dichloromethane. The acid chloride in some examples may be prepared in situ with cyanuric chloride and triethylamine in dichloromethane. Alternatively, a solution of the cyclic amine in a suitable organic solvent, such as dichloromethane, is treated with an appropriate base, such as triethylamine, followed by 2-5 equivalents of an appropriate isocyanate or acid chloride at 0° C.

The reaction is allowed to warm to room temperature and monitored by LCMS. Once complete the reaction mixture is quenched with water or sat. aq. NaHCO$_3$ and extracted with an organic solvent such as ethyl acetate or dichloromethane. The organic layers are dried (MgSO$_4$ or Na$_2$SO$_4$) and concentrated in vacuo. The residue is then purified by flash chromatography.

Step (d): Optional Protection/Deprotection

It will be understood that a reaction intermediate may be optionally protected and subsequently deprotected during the course of a reaction with one or more appropriately selected protecting groups. Suitable protecting groups will be known to those skilled in the art and are also described in *Protective Groups in Organic Synthesis,* 3rd Edition 1999 Greene T. W. and Wuts P. G. M., John Wiley & Sons, Inc. (see also 4th Edition 2007, John Wiley & Sons, Inc).

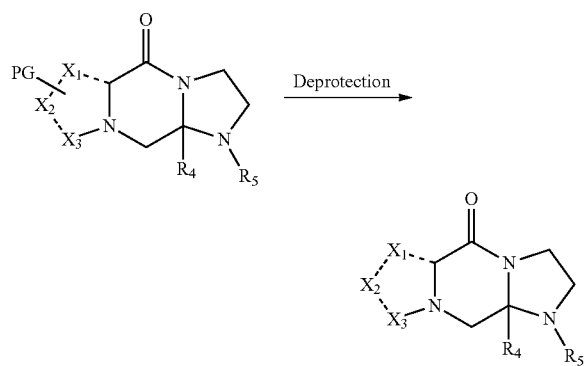

In general an appropriately protected fused ring system is dissolved in a mixture of solvents, for example, trifluoroacetic acid/dichloromethane in a 1:1-4:1 ratio where PG represents a protecting group which can be, but is not limited to, a (2-ethoxyethyl)(trimethyl)silane group. The reaction mixture is stirred at room temperature and monitored by LCMS. Once complete the mixture is concentrated in vacuo and the residue obtained is purified by flash chromatography.

General Method to Separate Stereoisomers by Chiral Chromatography

Selected compounds of the invention may be separated into single stereoisomers by HPLC using chromatographic columns with a chiral stationary phase. Suitable conditions to separate racemic compounds into enantiomers may include the conditions detailed below.

Column: Chiracel OD-H (250 mm×4.6 mm) 5 µM,
Isocratic Elution: Hexane:Ethanol (90:10 v/v)
Detector wavelength: 220 nm
Flow rate: 1.2 ml/min
Concentration: 1.0 mg/mL
Injection Volume: 10 µL
Column Temperature: 25° C.

In one embodiment the compounds of formula (I) may be prepared by a process involving the step of reacting a compound of formula (II) as defined above with a compound of general formula R'—C(C=O)R$_6$ wherein R' is a leaving group or an activated ester group. The compound of formula (II) may be in the form of a racemate or a single stereoisomer such as an enantiomer. Accordingly, the process of preparing a compound of formula (I) may involve the additional step(s) of forming and/or isolating stereoisomers, such as enantiomers, of a compound of formula (II) and reacting with a compound of formula R'—C(=O)R$_6$.

The leaving group may be any suitable known type such as those disclosed in J. March, *Advanced Organic Chemistry: Reactions, Mechanisms and Structure,* 4th Edition, pp 352-357, John Wiley & Sons, New York, 1992 which was incorporated herein by reference (see also 5th Edition, John Wiley & Sons, New York 2001 and 6th Edition, John Wiley & Sons, New Jersey, 2007). Preferably, the leaving group is halo, more preferably chloro.

The activated ester group will be known to those in the art, for example as described in Montalbetti, C. A. G. N., and Falque, V., *Tetrahedron* (2005) 61:10827-10852.

EXAMPLES

In order to exemplify the nature of the present invention such that it may be more clearly understood, the following non-limiting examples are provided. However, those skilled in the art will appreciate that the invention described herein is susceptible to variations and modifications other than those specifically described as follows.

Compound Synthesis $^1$H NMR spectra were recorded on either a Bruker Ultrashield™ 400 or AM 300 spectrometer. Spectra were recorded in CDCl$_3$, d$_6$-acetone, CD$_3$CN, CD$_3$OD or d$_6$-DMSO using the residual solvent peak as a reference. Chemical shifts are reported on the δ scale in parts per million (ppm) using the following conventions to assign the multiplicity: s (singlet), d (doublet), t (triplet), q (quartet), m (multiplet) and prefixed br (broad).

Mass spectra (ESI) were recorded on a Thermo Finnigan LCQ Advantage or LCQ Deca mass spectrometer coupled with a Thermo Finnigan Surveyor HPLC system. Unless stated otherwise, chromatography was performed with Phenomenex C8(2) or C18(2) columns. Water containing 0.1% formic acid (solvent A) and acetonitrile containing 0.1% formic acid (solvent B) were used for separations at acidic pH.

Ammonium acetate (5 mM, solvent A) and methanol (solvent B) were used for separations at neutral pH.

Flash chromatography was performed on 100-200 mesh silica gel or using a Biotage SP4 (GraceResolv™ Silica Flash cartridges or C18 silica cartridges plugged in). The abbreviations used in the Examples are as follows unless indicated otherwise:
DMF: N,N-dimethylformamide
DMSO: dimethylsulfoxide
ESI: electrospray ionisation
MS: mass spectrometry
LCMS: liquid chromatography coupled mass spectrometry
HPLC: high performance liquid chromatography
NMR: nuclear magnetic resonance
min: minute(s)
h: hour(s)

Examples

Synthesis of 11a-(4-methoxyphenyl)-1-[(3-methyl-1,2-oxazol-4-yl)carbonyl]-2,3,11,11a-tetrahydro-1H,5H-imidazo[1,2-a]thieno[3',2':4,5]pyrrolo[1,2-d]pyrazin-5-one (1)

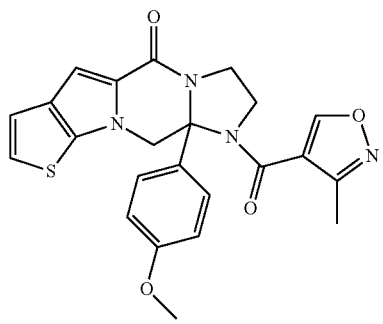 [SMILES: COc1ccc(C23Cn4c(cc5ccsc54)C(=O)N2CCN3C(=O)c2conc2C)cc1]

Step (a):
To a solution of methyl 6H-thieno[2,3-b]pyrrole-5-carboxylate (100 mg, 0.55 mmol) in DMF (2 mL) was added sodium hydride (15 mg, 0.63 mmol) at 0° C. The reaction mixture was stirred at 0° C. for 1 hour before 2-bromo-1-(4-methoxyphenyl)ethanone (251 mg, 1.1 mmol) was added. After 5 minutes, the reaction was allowed to warm to room temperature and stirred for 1 hour. The mixture was then poured into ice water and the resulting precipitate collected by filtration and washed with hexanes to yield methyl 6-[2-(4-methoxyphenyl)-2-oxoethyl]-6H-thieno[2,3-b]pyrrole-5-carboxylate (100 mg, 55% yield) as a white solid. ESI-MI m/z [M+H]$^+$ 330.15. $^1$H NMR (400 MHz, CDCl$_3$) δ 8.02 (d, J=8.8 Hz, 2H), 7.25 (s, 1H), 7.02 (d, J=5.3 Hz, 1H), 6.99 (d, J=8.8 Hz, 2H), 6.91 (d, J=5.3 Hz, 1H), 5.84 (s, 2H), 3.90 (s, 3H), 3.78 (s, 3H).

Step (b):
To a solution of methyl 6-[2-(4-methoxyphenyl)-2-oxoethyl]-6H-thieno[2,3-b]pyrrole-5-carboxylate (100 mg, 0.30 mmol) in 1,4-dioxane (10 mL) was added ethylenediamine (0.78 mL, 12 mmol) and the mixture heated at reflux. The reaction was monitored by LCMS. Upon completion, the reaction mixture was concentrated in vacuo and the residue purified by flash chromatography (1 to 6% methanol-dichloromethane) to yield 11a-(4-methoxyphenyl)-2,3,11,11a-tetrahydro-1H,5H-imidazo[1,2-a]thieno[3',2':4,5]pyrrolo[1,2-d]pyrazin-5-one (75 mg, 73% yield) as a white solid. ESI-MI m/z [M+H]$^+$ 340.25. $^1$H NMR (400 MHz, CDCl$_3$) δ 7.31 (d, J=8.7 Hz, 2H), 7.14 (s, 1H), 6.96 (d, J=5.3 Hz, 1H), 6.82 (d, J=5.3 Hz, 1H), 6.78 (d, J=8.7 Hz, 2H), 4.52 (d, J=11.7 Hz, 1H), 4.25 (d, J=11.7 Hz, 1H), 4.02-3.89 (m, 1H), 3.73 (s, 3H), 3.64-3.51 (m, 1H), 3.37-3.26 (m, 1H), 3.08-2.94 (m, 1H).

Step (c):
To generate the acid chloride: To a chilled (ice bath) suspension of 3-methylisoxazole-4-carboxylic acid (140 mg, 1.1 mmol) in dichloromethane (3 mL) was added oxalyl chloride (0.23 mL, 2.7 mmol) followed by DMF (1 drop, catalytic). The mixture was allowed to warm to room temperature and stirred until the reaction was complete (suspension dissolved). The resulting solution was concentrated in vacuo and further dried under a stream of nitrogen to yield the crude acid chloride.

To a chilled (ice bath) suspension of the acid chloride (generated as above, 1.1 mmol) in pyridine (2.4 mL) was added a suspension of 11a-(4-methoxyphenyl)-2,3,11,11a-tetrahydro-1H,5H-imidazo[1,2-a]thieno[3',2':4,5]pyrrolo[1,2-d]pyrazin-5-one (75 mg, 0.22 mmol) in pyridine (3 mL). The mixture was allowed to warm to room temperature. After 2 hours, LCMS indicated complete reaction so the mixture was diluted with water and extracted with ethyl acetate (×3). The extracts were combined, washed with brine, dried (Na$_2$SO$_4$), filtered and the filtrate concentrated in vacuo. The residue was purified by flash chromatography using the Biotage SP4 (0 to 10% methanol-ethyl acetate). The resulting material was dissolved in ethyl acetate and washed with sat. aq. NaHCO$_3$. The organic layer was concentrated in vacuo and resulting solid triturated with ethyl acetate-hexanes to yield 11a-(4-methoxyphenyl)-1-[(3-methyl-1,2-oxazol-4-yl)carbonyl]-2,3,11,11a-tetrahydro-1H,5H-imidazo[1,2-a]thieno[3',2':4,5]pyrrolo[1,2-d]pyrazin-5-one (1) (44 mg, 44% yield) as a solid. ESI-MI m/z [M+H]$^+$ 449.16. $^1$H NMR (400 MHz, CDCl$_3$) δ 8.54 (s, 1H), 7.35 (d, J=9.0 Hz, 2H), 7.14 (s, 1H), 6.98 (d, J=5.3 Hz, 1H), 6.90 (d, J=5.3 Hz, 1H), 6.78 (d, J=9.0 Hz, 2H), 5.71 (d, J=12.6 Hz, 1H), 4.62 (d, J=12.6 Hz, 1H), 4.44-4.30 (m, 1H), 4.09-4.01 (m, 1H), 3.94-3.79 (m, 2H), 3.73 (s, 3H), 2.46 (s, 3H).

Synthesis of 5a-(4-methoxyphenyl)-2-methyl-6-[(3-methyl-1,2-oxazol-4-yl)carbonyl]-5a,6,7,8-tetrahydro-5H-imidazo[1,2-a]imidazo[4',5':4,5]pyrrolo[1,2-d]pyrazin-10(1H)-one (2)

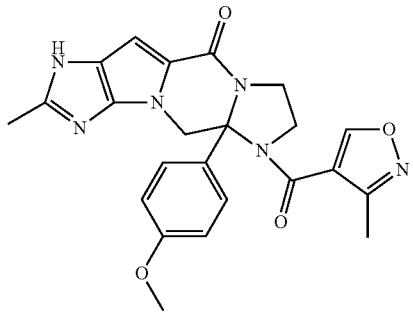 [SMILES: COc1ccc(C23Cn4c(cc5[nH]c(C)nc54)C(=O)N2CCN3C(=O)c2conc2C)cc1]

Either (5aS)-5a-(4-methoxyphenyl)-2-methyl-6-[(3-methyl-1,2-oxazol-4-yl)carbonyl]-1-{[2-(trimethylsilyl)ethoxy]methyl}-5a,6,7,8-tetrahydro-5H-imidazo[1,2-a]imidazo[4',5':4,5]pyrrolo[1,2-d]pyrazin-10(1H)-one or its regioisomer (5aS)-5a-(4-methoxyphenyl)-6-[(3-methyl-1,2-oxazol-4-yl)carbonyl]-3-{[2-(trimethylsilyl)ethoxy]methyl}-5a,6,7,8-tetrahydro-5H-imidazo[1,2-a]imidazo[4',5':4,5]pyrrolo[1,2-d]pyrazin-10(3H)-one (27 mg, 0.048 mmol) similarly prepared according to steps (a), (b) and (c) was dissolved in dichloromethane (0.9 mL) and treated with trifluoro acetic acid (2.1 mL). The mixture was stirred at room temperature. After one hour the LCMS indicated complete deprotection. The mixture was then concentrated in vacuo and the residue obtained purified by flash chromatography using the biotage SP4 (0-5% MeOH gradient in EtOAc) to yield either 5a-(4-methoxyphenyl)-2-methyl-6-[(3-methyl-1,2-oxazol-4-yl)carbonyl]-5a,6,7,8-tetrahydro-5H-imidazo[1,2-a]imidazo[4',5':4,5]pyrrolo[1,2-d]pyrazin-10(1H)-one (2) or its regioisomer 5a-(4-methoxyphenyl)-2-methyl-6-[(3-methyl-1,2-oxazol-4-yl)carbonyl]-5a,6,7,8-tetrahydro-5H-imidazo[1,2-a]imidazo[4',5':4,5]pyrrolo[1,2-d]pyrazin-10(3H)-one (8.5 mg, 40% yield). ESI-MI m/z [M+H]+ 447.09. $^1$H NMR (400 MHz, CDCl$_3$) δ 8.53 (br s, 1H), 8.46 (br s, 1H), 7.43 (br d, J=8.9 Hz, 2H), 6.82-6.73 (m, 2H), 6.69 (s, 1H), 6.05 (d, J=13.1 Hz, 1H), 4.46 (d, J=12.8 Hz, 1H), 4.35 (ddd, J=10.7, 8.8, 4.6 Hz, 1H), 4.00 (td, J=8.9, 5.6 Hz, 1H), 3.83 (tdd, J=13.2, 9.8, 6.6 Hz, 2H), 3.72 (s, 3H), 2.52 (s, 3H), 2.42 (d, J=0.5 Hz, 3H).

The compounds in Table 1 were similarly prepared by reference to the general method(s) and/or synthetic examples.

TABLE 1

Characterization of compound examples

| Compound Number | Name | ESI-MI m/z [M + H]+ | $^1$H NMR |
|---|---|---|---|
| 3 | 5a-(4-methoxyphenyl)-6-[(3-methyl-1,2-oxazol-4-yl)carbonyl]-5a,6,7,8-tetrahydro-5H,10H-furo[2',3':4,5]pyrrolo[1,2-a]imidazo[1,2-d]pyrazin-10-one | 433.14 | (400 MHz, CDCl$_3$) δ 8.53 (s, 1H), 7.46 (d, J = 2.2 Hz, 1H), 7.35 (d, J = 9.0 Hz, 2H), 6.83 (s, 1H), 6.79 (d, J = 9.0 Hz, 2H), 6.43 (dd, J = 2.2, 0.9 Hz, 1H), 5.68 (d, J = 12.6 Hz, 1H), 4.57 (d, J = 12.9 Hz, 1H), 4.44-4.30 (m, 1H), 4.08-3.98 (m, 1H), 3.89-3.78 (m, 2H), 3.74 (s, 3H), 2.46 (s, 3H). |
| 4 | 12a-(4-methoxyphenyl)-1-[(3-methyl-1,2-oxazol-4-yl)carbonyl]-2,3,12,12a-tetrahydro-1H,5H-imidazo[1',2':4,5]pyrazino[1,2-a]indol-5-one | 443.17 | (400 MHz, CDCl$_3$) δ 8.55 (s, 1H), 7.68 (d, J = 8.0 Hz, 1H), 7.41 (d, J = 8.4 Hz, 1H), 7.37-7.31 (m, 3H), 7.30 (s, 1H), 7.19-7.11 (m, 1H), 6.74 (d, J = 8.9 Hz, 2H), 5.99 (d, J = 12.6 Hz, 1H), 4.53 (d, J = 12.6 Hz, 1H), 4.49-4.36 (m, 1H), 4.16-4.03 (m, 1H), 3.94-3.80 (m, 2H), 3.70 (s, 3H), 2.47 (s, 3H). |
| 5 | 5a-(4-methoxyphenyl)-6-[(3-methyl-1,2-oxazol-4-yl)carbonyl]-5a,6,7,8-tetrahydro-5H,10H-imidazo[1,2-a]thieno[2',3':4,5]pyrrolo[1,2-d]pyrazin-10-one | 449.15 | (400 MHz, CDCl$_3$) δ 8.54 (s, 1H), 7.35 (d, J = 8.9 Hz, 2H), 7.30 (d, J = 5.4 Hz, 1H), 7.18 (s, 1H), 6.94 (d, J = 5.4 Hz, 1H), 6.78 (d, J = 9.0 Hz, 2H), 5.83 (d, J = 12.6 Hz, 1H), 4.61 (d, J = 12.6 Hz, 1H), 4.46-4.32 (m, 1H), 4.12-3.99 (m, 1H), 3.93-3.78 (m, 2H), 3.73 (s, 3H), 2.46 (s, 3H). |
| 6 | 11a-(4-fluorophenyl)-1-[(3-methyl-1,2-oxazol-4-yl)carbonyl]-2,3,11,11a-tetrahydro-1H,5H-imidazo[1,2-a]thieno[3',2':4,5]pyrrolo[1,2-d]pyrazin-5-one | 437.12 | (400 MHz, CDCl$_3$) δ 8.57 (s, 1H), 7.46-7.39 (m, 2H), 7.15 (s, 1H), 7.01-6.90 (m, 4H), 5.72 (d, 1H), 4.63 (d, J = 12.7 Hz, 1H), 4.47-4.38 (m, 1H), 4.15-4.03 (m, 1H), 3.90-3.80 (m, 2H), 2.46 (d, J = 0.5 Hz, 3H). |
| 7 | 1-[(3-methyl-1,2-oxazol-4-yl)carbonyl]-11a-(4-methylphenyl)-2,3,11,11a-tetrahydro-1H,5H-imidazo[1,2-a]thieno[3',2':4,5]pyrrolo[1,2-d]pyrazin-5-one | 433.13 | (400 MHz, CDCl$_3$) δ 8.53 (s, 1H), 7.32-7.28 (m, 2H), 7.14 (s, 1H), 7.08 (br d, J = 8.0 Hz, 2H), 7.01-6.96 (m, 1H), 6.92-6.88 (m, 1H), 5.73 (d, J = 12.7 Hz, 1H), 4.64 (d, J = 12.6 Hz, 1H), 4.43-4.34 (m, 1H), 4.09-4.02 (m, 1H), 3.92-3.80 (m, 2H), 2.46 (d, J = 0.5 Hz, 3H), 2.27 (s, 3H). |
| 8 | 12a-(4-methoxyphenyl)-1-[(3-methyl-1,2-oxazol-4-yl)carbonyl]-2,3,12,12a-tetrahydro-1H,5H-imidazo[1,2-a]pyrido[3',2':4,5]pyrrolo[1,2-d]pyrazin-5-one | 444.19 | (400 MHz, CDCl$_3$) δ 8.49 (br s, 1H), 8.44 (dd, J = 4.6, 1.6 Hz, 1H), 7.96 (dt, J = 4.7, 2.4 Hz, 1H), 7.37-7.45 (m, 2H), 7.18 (s, 1H), 7.10 (dd, J = 8.0, 4.6 Hz, 1H), 6.71-6.77 (m, 2H), 6.51 (d, J = 13.1 Hz, 1H), 4.37-4.49 (m, 2H), 4.04-4.13 (m, 1H), 3.96 (ddd, J = 11.3, 8.4, 5.7 Hz, 1H), 3.84-3.91 (m, 1H), 3.69 (s, 3H), 2.44 (s, 3H). |
| 9 | 12a-(4-methoxyphenyl)-1-[(3-methyl-1,2-oxazol-4-yl)carbonyl]-2,3,12,12a-tetrahydro-1H,5H-imidazo[1,2-a]pyrido[2',3':4,5]pyrrolo[1,2-d]pyrazin-5-one | 444.2 | (400 MHz, CDCl$_3$) δ 8.56 (s, 1H), 8.54 (dd, J = 4.5, 1.4 Hz, 1H), 7.76-7.68 (m, 1H), 7.47 (s, 1H), 7.36-7.31 (m, 2H), 7.24 (dd, J = 8.5, 4.5 Hz, 1H), 6.78-6.73 (m, 2H), 5.96 (d, J = 12.6 Hz, 1H), 4.59 (d, J = 12.7 Hz, 1H), 4.43 (ddd, J = 14.7, 11.1, 6.8 Hz, 1H), 4.09 (ddd, J = 9.1, 5.7, 2.8 Hz, 1H), 3.94-3.82 (m, 2H), 3.71 (s, 3H), 2.47 (d, J = 0.5 Hz, 3H). |

TABLE 1-continued

Characterization of compound examples

| Compound Number | Name | ESI-MI m/z [M + H]+ | 1H NMR |
|---|---|---|---|
| 10 | 1-[(3-methyl-1,2-oxazol-4-yl)carbonyl]-12a-(4-methylphenyl)-2,3,12,12a-tetrahydro-1H,5H-imidazo[1,2-a]pyrido[3',2':4,5]pyrrolo[1,2-d]pyrazin-5-one | 428.12 | (400 MHz, CDCl$_3$) δ 8.48 (s, 1H), 8.44 (dd, J = 4.6, 1.6 Hz, 1H), 7.96 (dd, J = 8.0, 1.6 Hz, 1H), 7.36 (d, J = 8.4 Hz, 2H), 7.19 (s, 1H), 7.10 (dd, J = 8.0, 4.6 Hz, 1H), 7.04 (d, J = 8.0 Hz, 2H), 6.52 (d, J = 13.1 Hz, 1H), 4.48 (d, J = 13.3 Hz, 1H), 4.45-4.38 (m, 1H), 4.08 (td, J = 9.1, 5.7 Hz, 1H), 3.96 (ddd, J = 11.4, 8.4, 5.7 Hz, 1H), 3.92-3.81 (m, 1H), 2.44 (d, J = 0.5 Hz, 3H), 2.23 (s, 3H). |
| 11 | 12a-(4-fluorophenyl)-1-[(3-methyl-1,2-oxazol-4-yl)carbonyl]-2,3,12,12a-tetrahydro-1H,5H-imidazo[1,2-a]pyrido[3',2':4,5]pyrrolo[1,2-d]pyrazin-5-one | 432.14 | (400 MHz, MeOD) δ 9.08 (s, 1H), 8.45-8.41 (m, 1H), 8.10 (d, J = 8.0 Hz, 1H), 7.52-7.44 (m, 2H), 7.23-7.16 (m, 2H), 6.98 (t, J = 8.7 Hz, 2H), 6.46 (d, J = 13.1 Hz, 1H), 4.57 (d, J = 13.1 Hz, 1H), 4.46-4.38 (m, 1H), 4.28-4.19 (m, 1H), 4.14-4.06 (m, 1H), 3.97 (dt, J = 11.6, 7.6 Hz, 1H), 2.38 (s, 3H). |
| 12 | 12a-(4-fluorophenyl)-1-[(3-methyl-1,2-oxazol-4-yl)carbonyl]-2,3,12,12a-tetrahydro-1H,5H-imidazo[1,2-a]pyrido[2',3':4,5]pyrrolo[1,2-d]pyrazin-5-one | 432.17 | (400 MHz, CDCl$_3$) δ 8.63-8.58 (m, 1H), 8.56-8.51 (m, 1H), 7.74-7.69 (m, 1H), 7.49-7.37 (m, 3H), 7.25-7.21 (m, 1H), 6.99-6.90 (m, 2H), 6.00-5.93 (m, 1H), 4.62-4.56 (m, 1H), 4.51-4.38 (m, 1H), 4.18-4.07 (m, 1H), 3.93-3.82 (m, 2H), 2.47 (s, 3H). |
| 13 | 1-[(3-methyl-1,2-oxazol-4-yl)carbonyl]-11a-(6-methylpyridin-3-yl)-2,3,11,11a-tetrahydro-1H,5H-imidazo[1,2-a]thieno[3',2':4,5]pyrrolo[1,2-d]pyrazin-5-one | 434.14 | (400 MHz, CDCl$_3$) δ 8.62 (d, J = 0.5 Hz, 1H), 8.52 (d, J = 2.3 Hz, 1H), 7.52 (dd, J = 8.3, 2.7 Hz, 1H), 7.15 (s, 1H), 7.05 (d, J = 8.3 Hz, 1H), 6.99 (d, J = 5.3 Hz, 1H), 6.93 (d, J = 5.3 Hz, 1H), 5.72 (d, J = 12.7 Hz, 1H), 4.56 (d, J = 12.8 Hz, 1H), 4.47 (ddd, J = 11.9, 8.6, 4.0 Hz, 1H), 4.11 (ddd, J = 8.6, 8.1, 5.4 Hz, 1H), 3.95 (ddd, J = 9.4, 8.2, 4.0 Hz, 1H), 3.80 (dt, J = 11.7, 8.1 Hz, 1H), 2.47 (s, 3H), 2.45 (s, 3H). |
| 14 | 1-(cyclohexylcarbonyl)-11a-(4-fluorophenyl)-2,3,11,11a-tetrahydro-1H,5H-imidazo[1,2-a]thieno[3',2':4,5]pyrrolo[1,2-d]pyrazin-5-one | 438 | (400 MHz, CDCl$_3$) δ 7.43-7.30 (m, 2H), 7.12 (s, 1H), 7.04-6.77 (m, 4H), 5.67 (d, J = 12.8 Hz, 1H), 4.51-4.33 (m, 2H), 4.03 (d, J = 6.4 Hz, 1H), 3.76 (s, 2H), 2.45-2.29 (m, 1H), 1.84 (d, J = 10.8 Hz, 3H), 1.73 (s, 2H), 1.47 (d, J = 11.8 Hz, 1H), 1.28 (d, J = 6.9 Hz, 4H). |
| 15 | 11a-(4-fluorophenyl)-1-(furan-2-ylcarbonyl)-2,3,11,11a-tetrahydro-1H,5H-imidazo[1,2-a]thieno[3',2':4,5]pyrrolo[1,2-d]pyrazin-5-one | 422.05 | (400 MHz, CDCl$_3$) δ 7.59 (s, 1H), 7.40 (dd, J = 8.0, 5.1 Hz, 2H), 7.27-7.19 (m, 1H), 7.15 (s, 1H), 7.06-6.83 (m, 4H), 6.58 (s, 1H), 5.78 (d, J = 12.7 Hz, 1H), 4.58 (d, J = 12.8 Hz, 1H), 4.50 (d, J = 5.7 Hz, 2H), 4.29 (t, J = 7.7 Hz, 1H), 3.83 (d, J = 7.2 Hz, 1H). |
| 16 | 1-(cyclopropylcarbonyl)-11a-(4-fluorophenyl)-2,3,11,11a-tetrahydro-1H,5H-imidazo[1,2-a]thieno[3',2':4,5]pyrrolo[1,2-d]pyrazin-5-one | 396.1 | (400 MHz, CDCl$_3$) δ 7.59 (s, 1H), 7.40 (dd, J = 8.0, 5.1 Hz, 2H), 7.27-7.19 (m, 1H), 7.15 (s, 1H), 7.06-6.83 (m, 4H), 6.58 (s, 1H), 5.78 (d, J = 12.7 Hz, 1H), 4.58 (d, J = 12.8 Hz, 1H), 4.50 (d, J = 5.7 Hz, 2H), 4.29 (t, J = 7.7 Hz, 1H), 3.83 (d, J = 7.2 Hz, 1H). |
| 17 | 11a-(4-fluorophenyl)-1-(2-methylpropanoyl)-2,3,11,11a-tetrahydro-1H,5H-imidazo[1,2-a]thieno[3',2':4,5]pyrrolo[1,2-d]pyrazin-5-one | 465 | (400 MHz, CDCl$_3$) δ 7.35 (dd, J = 8.4, 5.0 Hz, 2H), 7.11 (s, 1H), 7.02-6.76 (m, 4H), 5.66 (d, J = 12.8 Hz, 1H), 4.42 (dd, J = 17.8, 11.4 Hz, 2H), 4.00 (t, J = 9.7 Hz, 1H), 3.83-3.66 (m, 2H), 2.67 (dd, J = 13.3, 6.6 Hz, 1H), 1.20 (d, J = 6.6 Hz, 3H), 1.12 (d, J = 6.7 Hz, 3H). |

TABLE 1-continued

Characterization of compound examples

| Compound Number | Name | ESI-MI m/z [M + H]+ | 1H NMR |
|---|---|---|---|
| 18 | 11a-(4-fluorophenyl)-1-[(5-methyl-1,2-oxazol-3-yl)carbonyl]-2,3,11,11a-tetrahydro-1H,5H-imidazo[1,2-a]thieno[3',2':4,5]pyrrolo[1,2-d]pyrazin-5-one | 437.1 | (400 MHz, CDCl₃) δ 7.35 (dd, J = 8.4, 5.0 Hz, 2H), 7.11 (s, 1H), 7.02-6.76 (m, 4H), 5.66 (d, J = 12.8 Hz, 1H), 4.42 (dd, J = 17.8, 11.4 Hz, 2H), 4.00 (t, J = 9.7 Hz, 1H), 3.83-3.66 (m, 2H), 2.67 (dd, J = 13.3, 6.6 Hz, 1H), 1.20 (d, J = 6.6 Hz, 3H), 1.12 (d, J = 6.7 Hz, 3H). |
| 19 | l-(cyclohexylacetyl)-11a-(4-fluorophenyl)-2,3,11,11a-tetrahydro-1H,5H-imidazo[1,2-a]thieno[3',2':4,5]pyrrolo[1,2-d]pyrazin-5-one | 452.15 | (400 MHz, CDCl₃) δ 7.35 (dd, J = 8.4, 5.0 Hz, 2H), 7.11 (s, 1H), 7.02-6.76 (m, 4H), 5.66 (d, J = 12.8 Hz, 1H), 4.42 (dd, J = 17.8, 11.4 Hz, 2H), 4.00 (t, J = 9.7 Hz, 1H), 3.83-3.66 (m, 2H), 2.67 (dd, J = 13.3, 6.6 Hz, 1H), 1.20 (d, J = 6.6 Hz, 3H), 1.12 (d, J = 6.7 Hz, 3H). |
| 20 | 1-[(3-tert-butyl-1-methyl-1H-pyrazol-5-yl)carbonyl]-11a-(4-fluorophenyl)-2,3,11,11a-tetrahydro-1H,5H-imidazo[1,2-a]thieno[3',2':4,5]pyrrolo[1,2-d]pyrazin-5-one | 492.15 | (400 MHz, CDCl₃) δ 7.49-7.37 (m, 2H), 7.15 (s, 1H), 6.96 (dt, J = 14.0, 5.1 Hz, 4H), 6.27 (s, 1H), 5.73 (d, J = 12.7 Hz, 1H), 4.65 (d, J = 12.6 Hz, 1H), 4.39-4.26 (m, 1H), 4.16 (dd, J = 13.9, 8.5 Hz, 1H), 3.96 (s, 3H), 3.93-3.75 (m, 2H), 1.30 (s, 9H). |
| 21 | 11a-(4-fluorophenyl)-1-[(5-methyl-1,3-oxazol-4-yl)carbonyl]-2,3,11,11a-tetrahydro-1H,5H-imidazo[1,2-a]thieno[3',2':4,5]pyrrolo[1,2-d]pyrazin-5-one | 437.15 | (400 MHz, CDCl₃) δ 7.49-7.37 (m, 2H), 7.15 (s, 1H), 6.96 (dt, J = 14.0, 5.1 Hz, 4H), 6.27 (s, 1H), 5.73 (d, J = 12.7 Hz, 1H), 4.65 (d, J = 12.6 Hz, 1H), 4.39-4.26 (m, 1H), 4.16 (dd, J = 13.9, 8.5 Hz, 1H), 3.96 (s, 3H), 3.93-3.75 (m, 2H), 1.30 (s, 9H). |
| 22 | 11a-(4-fluorophenyl)-1-(furan-2-ylacetyl)-2,3,11,11a-tetrahydro-1H,5H-imidazo[1,2-a]thieno[3',2':4,5]pyrrolo[1,2-d]pyrazin-5-one | 451 | (400 MHz, CDCl₃) δ 7.49-7.37 (m, 2H), 7.15 (s, 1H), 6.96 (dt, J = 14.0, 5.1 Hz, 4H), 6.27 (s, 1H), 5.73 (d, J = 12.7 Hz, 1H), 4.65 (d, J = 12.6 Hz, 1H), 4.39-4.26 (m, 1H), 4.16 (dd, J = 13.9, 8.5 Hz, 1H), 3.96 (s, 3H), 3.93-3.75 (m, 2H), 1.30 (s, 9H). |
| 23 | N-benzyl-11a-(4-fluorophenyl)-5-oxo-2,3,11,11a-tetrahydro-1H,5H-imidazo[1,2-a]thieno[3',2':4,5]pyrrolo[1,2-d]pyrazine-1-carboxamide | 461 | (400 MHz, CDCl₃) δ 7.49-7.37 (m, 2H), 7.15 (s, 1H), 6.96 (dt, J = 14.0, 5.1 Hz, 4H), 6.27 (s, 1H), 5.73 (d, J = 12.7 Hz, 1H), 4.65 (d, J = 12.6 Hz, 1H), 4.39-4.26 (m, 1H), 4.16 (dd, J = 13.9, 8.5 Hz, 1H), 3.96 (s, 3H), 3.93-3.75 (m, 2H), 1.30 (8, 9H). |
| 24 | N-cyclohexyl-11a-(4-fluorophenyl)-5-oxo-2,3,11,11a-tetrahydro-1H,5H-imidazo[1,2-a]thieno[3',2':4,5]pyrrolo[1,2-d]pyrazine-1-carboxamide | 453.15 | (400 MHz, CDCl₃) δ 7.41 (dd, J = 8.2, 5.1 Hz, 2H), 7.10 (s, 1H), 7.03-6.75 (m, 3H), 5.62 (d, J = 12.8 Hz, 1H), 4.49 (d, J = 12.8 Hz, 1H), 4.46-4.36 (m, 1H), 4.25 (d, J = 7.1 Hz, 1H), 3.73 (ddd, J = 28.2, 21.7, 7.2 Hz, 2H), 3.61-3.37 (m, 1H), 1.96 (d, J = 12.8 Hz, 2H), 1.82-1.62 (m, 3H), 1.47-1.00 (m, 7H). |
| 25 | 11a-(4-fluorophenyl)-1-(phenylsulfonyl)-2,3,11,11a-tetrahydro-1H,5H-imidazo[1,2-a]thieno[3',2':4,5]pyrrolo[1,2-d]pyrazin-5-one | 468.15 | (400 MHz, CDCl₃) δ 7.58-7.45 (m, 3H), 7.43-7.34 (m, 2H), 7.35-7.28 (m, 2H), 7.02 (s, 1H), 6.94 (dd, J = 14.4, 5.3 Hz, 2H), 6.89-6.81 (m, 2H), 5.53 (d, J = 12.7 Hz, 1H), 4.60 (d, J = 12.7 Hz, 1H), 4.25-4.11 (m, 1H), 4.00-3.81 (m, 2H), 3.64-3.51 (m, 1H). |
| 26 | 1-(benzylsulfonyl)-11a-(4-fluorophenyl)-2,3,11,11a-tetrahydro-1H,5H-imidazo[1,2-a]thieno[3',2':4,5]pyrrolo[1,2-d]pyrazin-5-one | 482 | (400 MHz, CDCl₃) δ 7.58-7.45 (m, 3H), 7.43-7.34 (m, 2H), 7.35-7.28 (m, 2H), 7.02 (s, 1H), 6.94 (dd, J = 14.4, 5.3 Hz, 2H), 6.89-6.81 (m, 2H), 5.53 (d, J = 12.7 Hz, 1H), 4.60 (d, J = 12.7 Hz, 1H), 4.25-4.11 (m, 1H), 4.00-3.81 (m, 2H), 3.64-3.51 (m, 1H). |

TABLE 1-continued

Characterization of compound examples

| Compound Number | Name | ESI-MI m/z [M + H]+ | 1H NMR |
|---|---|---|---|
| 27 | 11a-(4-fluorophenyl)-1-[(4-nitrophenyl)sulfonyl]-2,3,11,11a-tetrahydro-1H,5H-imidazo[1,2-a]thieno[3',2':4,5]pyrrolo[1,2-d]pyrazin-5-one | 513 | (400 MHz, $CDCl_3$) δ 7.58-7.45 (m, 3H), 7.43-7.34 (m, 2H), 7.35-7.28 (m, 2H), 7.02 (s, 1H), 6.94 (dd, J = 14.4, 5.3 Hz, 2H), 6.89-6.81 (m, 2H), 5.53 (d, J = 12.7 Hz, 1H), 4.60 (d, J = 12.7 Hz, 1H), 4.25-4.11 (m, 1H), 4.00-3.81 (m, 2H), 3.64-3.51 (m, 1H). |

Biological Data

The in vivo and in vitro antiviral activity of the compounds of the invention may be determined using the following methods.

RSV Antiviral Assay Protocol

Compounds of the invention were tested for their antiviral activity against respiratory syncytial virus. Cytopathic effect (CPE) assays were performed essentially as described in the literature (see, for example, Watanabe et al, 1994, J. *Virological Methods*, 48:257). Serial dilutions of the test compounds were made in 96 well plates. HEp2 cells ($1.0 \times 10^4$ cells/well) were infected with RSV at a low multiplicity of infection (e.g. RSV A2 at an moi of ~0.01) and added to plates to assess antiviral activity. Uninfected HEp2 cells were used to assess compound cytotoxicity. Assays were incubated for 5 days at 37° C. in a 5% $CO_2$ atmosphere. The extent of CPE was determined via metabolism of the vital dye 3-(4,5-dimethylthiaxol-2-yl)-2,5-diphenyltetrazolium bromide (MTT). MTT (1 mg/ml) was added to each well and plates incubated for 2 hours incubation at 37° C. Wells were aspirated, isopropanol (200 μL) was added and absorbance values read at 540/650 nm. Compound concentrations that inhibited CPE by 50% ($EC_{50}$) and developed cytotoxicity ($CC_{50}$) were calculated using non-linear regression analysis.

Representative activity ranges for compounds of the invention against RSV A2 are shown in Table 2 where RSV A2 $EC_{50}$ mean values lie in the ranges A: ≤0.049 μM, B: 0.05-0.099 μM, C: 0.10-0.499 μM, D: 0.5-10.0 μM and E: >10.0 μM. In the inventors' experience, replicate $EC_{50}$ values usually fall within three standard deviations of the mean.

TABLE 2

RSV A2 antiviral data for compounds

| No. | Activity Range | No. | Activity Range | No. | Activity Range |
|---|---|---|---|---|---|
| 1 | A | 2 | A | 3 | B |
| 4 | A | 5 | C | 6 | A |
| 7 | A | 8 | A | 9 | C |
| 10 | A | 11 | A | 12 | C |
| 13 | A | 14 | E | 15 | E |
| 16 | E | 17 | E | 18 | E |
| 19 | E | 20 | E | 21 | C |
| 22 | E | 23 | E | 24 | E |
| 25 | E | 26 | E | 27 | D |

RSV Fusion Assay

Selected compounds of the invention can be tested for their ability to inhibit the essential fusion processes of the respiratory syncytial virus.

Generation of RSV-F Constructs

Single-stranded synthetic DNA oligonucleotides encoding the portions of RSV A2 F glycoprotein incorporating optimal codons and without potential poly(A) addition or splice sites were generated synthetically (Mason et al, WO02/42326). A membrane-anchored full-length F was generated essentially according to the method described therein and in Morton et al, 2003, *Virology*, 311:275.

Syncytium Formation Assay

Fusion activity of the RSV-F constructs was measured in 293 cells essentially according to the method described in Morton et al. For example: cells in six well plates at approximately 80% confluency were transfected by adding plasmid DNA (0.5-1.5 μg/well) carrying the constructs of interest in $CaPO_4$ solution for 2 hours. After glycerol shock and wash, the transfected cells were trypsinized and $4\text{-}10 \times 10^4$ cells/well added to 96-well plates containing 2-fold or 3-fold serial dilutions of the test compound. Syncytium formation was evaluated by visual inspection and quantified at 42 hours post-transfection by addition of 20 μL of CellTiter 96 One Solution (Promega) followed by incubation for 2 hours at 37° C. The absorbance values read at 490/690 nm. The compound concentration that reduced absorbance relative to untreated control cultures by 50% ($EC_{50}$) was calculated using non-linear regression analysis.

RSV Cotton Rat Model

The cotton rat model may be performed essentially as described in the literature (Wyde et al, 2003, Antiviral Res., 60:221). Briefly, cotton rats weighing 50-100 g are lightly anesthetized with isoflurane and dosed orally with 100 mg/kg/day of compound or vehicle control. Viral infection follows 2 hours post-treatment in similarly anesthetized rats by intranasal instillation with approximately 1000 $TCID_{50}$ of RSV A2 per animal. Four days after virus inoculation, each cotton rat is sacrificed and their lungs removed and RSV titres determined by plaque assay.

RSV Balb/c Mouse Model

The mouse model may be performed essentially as described by Cianci et al, 2004, Antimicrobial Agents and Chemotherapy, 48:413. Briefly, eight week old female Balb/c mice are weighed, anesthetized intraperitoneally with Avertin™ and compound or vehicle administered orally preinfection and subsequently on a daily or twice daily basis. Mice are inoculated intranasally with approximately 10000 $TCID_{50}$ RSV A2 per animal. Three days after virus inoculation, each mouse is sacrificed and their lungs removed and RSV titres determined by plaque assay. Body weights, spleen and liver weights can also be assessed. In addition, the ability of a test compound to reduce total and differential (macrophages, neutrophils and lymphocytes) inflammatory cell counts in bronchoalveolar lavage fluid (BALF) can also be measured. This allows a study of the ability of the test compound to ameliorate the inflammatory response to RSV infection in animals treated with compound compared with those only inoculated with RSV.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is known, is not, and should not be taken as an acknowledgement or admission or any form of suggestion that that prior publication, or information derived from it, or known matter forms part of the common general knowledge in the field of endeavour to which this specification relates.

It will be understood to persons skilled in the art of the invention that many modifications may be made without departing from the spirit and scope of the invention.

The invention claimed is:

1. A compound of formula (I)

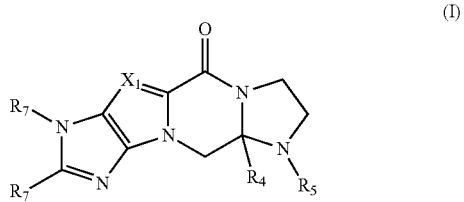

(I)

wherein
$X_1$ is $CR_3$;
$R_3$ is H;
$R_4$ is $C_{1-6}$alkyl, $C_{2-6}$alkenyl, $C_{2-6}$alkynyl, $C_{3-8}$cycloalkyl, heterocyclyl or aryl, wherein the alkyl, alkenyl, alkynyl, cycloalkyl, heterocyclyl and aryl is optionally substituted with one or more substituents selected from the group consisting of $C_{1-6}$alkyl, $C_{2-6}$alkenyl, $C_{2-6}$alkynyl, $C_{3-6}$cycloalkyl, 5-membered heterocyclyl, 6-membered heterocyclyl, aryl, halo, $C_{1-6}$alkylhalo, $C_{1-6}$alkylhydroxy, $C_{1-6}$alkoxy, $C_{1-6}$alkoxyhalo, oxo, acyl, carboxylate, cyano, nitro, amino, amido, aminoacyl, thiol, $C_{1-6}$alkylthio, thioxo, sulfate, sulfonate, sulfonyl, sulfonamido;
$R_5$ is $R_6$, C(=O)$R_6$, C(=S)$R_6$ or S(O)$_2R_6$;
$R_6$ is $C_{1-6}$alkyl, $C_{2-6}$alkenyl, $C_{2-6}$alkynyl, $C_{3-8}$cycloalkyl, heterocyclyl, aryl, N(R")$_2$, (NR")$_q$(R''')$_q C_{3-8}$cycloalkyl, (NR")$_q$(R''')$_q$heterocyclyl or (NR")$_q$(R''')$_q$aryl, wherein (i) each R" is H, $C_{1-6}$alkyl, $C_{2-6}$alkenyl, $C_{2-6}$alkynyl, $C_{3-8}$cycloalkyl, heterocyclyl or aryl, (ii) each R''' is $C_{1-6}$alkyl, $C_{2-6}$alkenyl, $C_{2-6}$alkynyl, $C_{3-8}$cycloalkyl, heterocyclyl or aryl, and (iii) each q is independently 0 or 1, and further wherein each alkyl, alkenyl, alkynyl, cycloalkyl, heterocyclyl and aryl is optionally substituted with one or more substituents selected from the group consisting of $C_{1-6}$alkyl, $C_{2-6}$alkenyl, $C_{2-6}$alkynyl, $C_{3-6}$cycloalkyl, 5-membered heterocyclyl, 6-membered heterocyclyl, aryl, halo, $C_{1-6}$alkyl halo, hydroxy, $C_{1-6}$alkylhydroxy, $C_{1-6}$alkoxy, $C_{1-6}$alkoxyhalo, oxo, acyl, carboxy, cyano, nitro, amino, amido, aminoacyl, thiol, $C_{1-6}$alkylthio, thioxo, sulfate, sulfonate, sulfinyl, sulfonyl and sulfonamide; and
each $R_7$ is H, $C_{1-6}$alkyl, $C_{2-6}$alkenyl, $C_{2-6}$alkynyl, halo, $C_{1-6}$alkylhalo, hydroxy, $C_{1-6}$alkylhydroxy, $C_{1-6}$alkoxy, $C_{1-6}$alkoxyhalo, C(O)H, C(O)$C_{1-6}$alkyl, C(O)$_2$H, C(O)$_2C_{1-6}$alkyl, cyano, nitro, NH$_2$, NH(C$_{1-6}$alkyl), N(C$_{1-6}$alkyl)$_2$, NHC(O)H, NHC(O)C$_{1-6}$alkyl, NHC(O)$_2$C$_{1-6}$alkyl, NHS(O)$_2$C$_{1-6}$alkyl, C(O)NH$_2$, C(O)NH(C$_{1-6}$alkyl), C(O)N(C$_{1-6}$alkyl)$_2$, SH, C$_{1-6}$alkylthio, S(O)$_3$H, S(O)$_3$C$_{1-6}$alkyl, S(O)H, S(O)C$_{1-6}$alkyl, S(O)$_2$H, S(O)$_2$C$_{1-6}$alkyl, S(O)$_2$NH$_2$, S(O)$_2$NHC$_{1-6}$alkyl, S(O)$_2$N(C$_{1-6}$alkyl)$_2$, C$_{3-6}$cycloalkyl, heterocyclyl, aryl or heteroaryl, wherein each alkyl, alkenyl, alkynyl, cycloalkyl, heterocyclyl, aryl and heteroaryl is optionally and independently substituted with one or more substituents selected from the group consisting of $C_{1-6}$alkyl, $C_{2-6}$alkenyl, $C_{2-6}$alkynyl, $C_{3-6}$cycloalkyl, 5-membered heterocyclyl, 6-membered heterocyclyl, aryl, halo, $C_{1-6}$alkyl halo, hydroxy, $C_{1-6}$alkylhydroxy, $C_{1-6}$alkoxy, $C_{1-6}$alkoxyhalo, oxo, acyl, carboxy, cyano, nitro, amino, amido, aminoacyl, thiol, $C_{1-6}$alkylthio, thioxo, sulfate, sulfonate, sulfinyl, sulfonyl and sulfonamide;

or pharmaceutically acceptable salts, racemates, stereoisomers and/or tautomers thereof.

2. The compound according to claim 1, wherein
$R_4$ is optionally substituted heterocyclyl or optionally substituted aryl;
$R_5$ is C(=O)$R_6$ or S(O)$_2R_6$; and
$R_6$ is optionally substituted $C_{1-4}$alkyl, optionally substituted $C_{3-6}$cycloalkyl, optionally substituted heterocyclyl, optionally substituted aryl, optionally substituted (NR")$_q$(R''')$_q C_{3-6}$cycloalkyl, optionally substituted (NR")$_q$(R''')$_q$heterocyclyl or optionally substituted (NR")$_q$(R''')$_q$aryl, wherein (i) R" is H, (ii) R''' is optionally substituted $C_{1-3}$alkyl, and (iii) each q is independently 0 or 1;
or pharmaceutically acceptable salts, racemates, stereoisomers and/or tautomers thereof.

3. The compound according to claim 1, wherein $R_4$ is optionally substituted phenyl or optionally substituted 6-membered heteroaryl selected from the group consisting of pyridinyl, pyridazinyl, pyrimidinyl and pyrazinyl.

4. The compound according to claim 3, wherein $R_4$ is para-substituted phenyl.

5. The compound according to claim 1, wherein:
(i) $R_5$ is C(=O)$R_6$, wherein $R_6$ is optionally substituted $C_{1-4}$alkyl, optionally substituted $C_{3-6}$cycloalkyl, optionally substituted heterocyclyl, optionally substituted aryl, optionally substituted NH—$C_{3-6}$cycloalkyl, optionally substituted CH$_2$—$C_{3-6}$cycloalkyl, optionally substituted NH-heteroaryl, optionally substituted CH$_2$-heteroaryl, optionally substituted NH-aryl or optionally substituted CH$_2$-aryl; or
(ii) $R_5$ is S(O)$_2R_6$, wherein $R_6$ is optionally substituted aryl or optionally substituted CH$_2$-aryl; and
further wherein each occurrence of aryl is optionally substituted phenyl and each occurrence of heteroaryl is optionally substituted 5-membered heteroaryl containing one, two or three oxygen, nitrogen and/or sulfur heteroatoms or optionally substituted 6-membered heteroaryl containing one or two nitrogen heteroatoms.

6. The compound according to claim 1, wherein $R_5$ is C(=O)$R_6$.

7. The compound according to claim 1, wherein each occurrence of aryl is optionally substituted phenyl and each occurrence of heteroaryl is optionally substituted 5-membered heteroaryl containing one, two or three oxygen, nitrogen and/or sulfur heteroatoms or optionally substituted 6-membered heteroaryl containing one or two nitrogen heteroatoms.

8. The compound according to claim 1, wherein the compound is a single stereoisomeric form.

9. The compound according to claim 8, wherein the single stereoisomeric form is represented by formula (I')

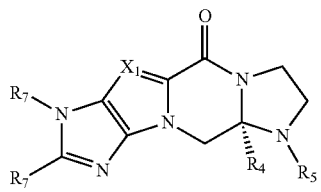

(I')

or pharmaceutically acceptable salts thereof.

10. The compound according to claim 1, wherein the compound is:
   2) 5a-(4-methoxyphenyl)-2-methyl-6-[(3-methyl-1,2-oxazol-4-yl)carbonyl]-5a,6,7,8-tetrahydro-5H-imidazo[1,2-a]imidazo[4',5':4,5]pyrrolo[1,2-d]pyrazin-10(1H)-one;

or pharmaceutically acceptable salts, racemates or enantiomers thereof.

11. A pharmaceutical composition comprising a compound according to claim 1 or pharmaceutically acceptable salts, racemates, stereoisomers or tautomers thereof and a pharmaceutically acceptable carrier.

12. A respiratory syncytial virus antiviral composition comprising a compound according to claim 1 or pharmaceutically acceptable salts, racemates, stereoisomers or tautomers thereof, together with a pharmaceutically acceptable carrier and one or more respiratory syncytial virus antiviral agents.

13. A method of modulating respiratory syncytial virus viral activity in a subject comprising administering to said subject a therapeutically effective amount of a compound according to claim 1 or pharmaceutically acceptable salts, racemates, stereoisomers or tautomers thereof.

14. A method of modulating respiratory syncytial virus viral activity in a subject comprising the step of administering to said subject a therapeutically effective amount of a pharmaceutical composition according to claim 11.

15. A process for preparing a compound of formula (I)

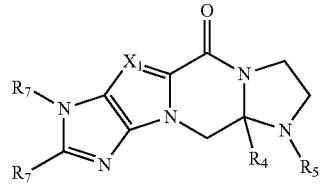

(I)

or a pharmaceutically acceptable salt thereof,
wherein
$R_5$ is $C(=O)R_6$; and
$X_1$, $R_4$, $R_6$ and $R_7$ are as defined in claim 1;
comprising:
(i) reacting a compound of formula (II)

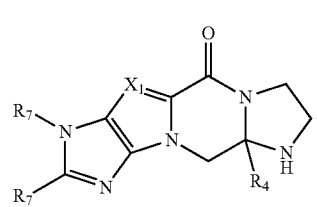

(II)

wherein $X_1$, $R_4$ and $R_7$ are as defined in claim 1;

with a compound of formula $R'-C(=O)R_6$, wherein
R' is halo; and
$R_6$ is as defined in claim 1;
to provide a compound of formula (I) and
(ii) optionally converting the compound of formula (I) into a pharmaceutically acceptable salt thereof.

16. A compound of formula (II)

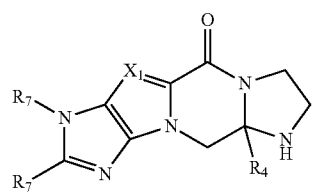

(II)

wherein
$X_1$ is $CR_3$;
$R_3$ is H;
$R_4$ is $C_{1-6}$alkyl, $C_{2-6}$alkenyl, $C_{2-6}$alkynyl, $C_{3-8}$cycloalkyl, heterocyclyl or aryl, wherein the alkyl, alkenyl, alkynyl, cycloalkyl, heterocyclyl and aryl is optionally substituted with one or more substituents selected from the group consisting of $C_{1-6}$alkyl, $C_{2-6}$alkenyl, $C_{2-6}$alkynyl, $C_{3-6}$cycloalkyl, 5-membered heterocyclyl, 6-membered heterocyclyl, aryl, halo, $C_{1-6}$alkylhalo, $C_{1-6}$alkylhydroxy, $C_{1-6}$alkoxy, $C_{1-6}$alkoxyhalo, oxo, acyl, carboxylate, cyano, nitro, amino, amido, aminoacyl, thiol, $C_{1-6}$alkylthio, thioxo, sulfate, sulfonate, sulfonyl, sulfonyl and sulfonamido; and each $R_7$ is H, $C_{1-6}$alkyl, $C_{2-6}$alkenyl, $C_{2-6}$alkynyl, halo, $C_{1-6}$alkylhalo, hydroxy, $C_{1-6}$alkylhydroxy, $C_{1-6}$alkoxy, $C_{1-6}$alkoxyhalo, $C(O)H$, $C(O)C_{1-6}$alkyl, $C(O)_2H$, $C(O)_2C_{1-6}$alkyl, cyano, nitro, $NH_2$, $NH(C_{1-6}$alkyl), $N(C_{1-6}$alkyl)$_2$, $NHC(O)H$, $NHC(O)C_{1-6}$alkyl, $NHC(O)_2C_{1-6}$alkyl, $NHS(O)_2C_{1-6}$alkyl, $C(O)NH_2$, $C(O)NH(C_{1-6}$alkyl), $C(O)N(C_{1-6}$alkyl)$_2$, SH, $C_{1-6}$alkylthio, $S(O)_3H$, $S(O)_3C_{1-6}$alkyl, $S(O)H$, $S(O)C_{1-6}$alkyl, $S(O)_2H$, $S(O)_2C_{1-6}$alkyl, $S(O)_2NH_2$, $S(O)_2NHC_{1-6}$alkyl, $S(O)_2N(C_{1-6}$alkyl)$_2$, $C_{3-6}$cycloalkyl, heterocyclyl, aryl or heteroaryl, wherein each alkyl, alkenyl, alkynyl, cycloalkyl, heterocyclyl, aryl and heteroaryl is optionally and independently substituted with one or more substituents selected from the group consisting of $C_{1-6}$alkyl, $C_{2-6}$alkenyl, $C_{2-6}$alkynyl, $C_{3-6}$cycloalkyl, 5-membered heterocyclyl, 6-membered heterocyclyl, aryl, halo, $C_{1-6}$alkyl halo, hydroxy, $C_{1-6}$alkylhydroxy, $C_{1-6}$alkoxy, $C_{1-6}$alkoxyhalo, oxo, acyl, carboxy, cyano, nitro, amino, amido, aminoacyl, thiol, $C_{1-6}$alkylthio, thioxo, sulfate, sulfonate, sulfinyl, sulfonyl and sulfonamide;

or pharmaceutically acceptable salts, racemates, stereoisomers and/or tautomers thereof.

17. The compound according to claim 16, wherein the compound is a single stereoisomeric form.

18. A process for preparing a compound of formula (II)
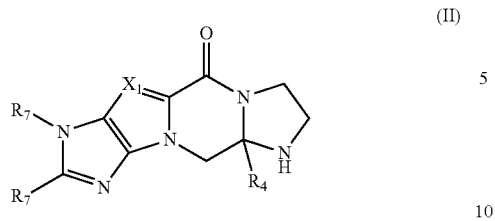
(II)
wherein
$X_1$, $R_4$ and $R_7$ are as defined in claim 16;
comprising:
 reacting a compound of formula (III)
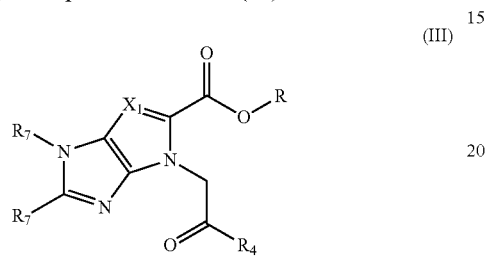
(III)
wherein
R is H or $C_{1-6}$alkyl; and
$X_1$, $R_4$ and $R_7$ are as defined in claim 16;
with ethylenediamine in an inert solvent and optionally in the presence of an acetic acid catalyst.
* * * * *